US010502665B2

(12) United States Patent
Milton et al.

(10) Patent No.: US 10,502,665 B2
(45) Date of Patent: Dec. 10, 2019

(54) AEROSOL COLLECTION SYSTEM AND METHOD

(71) Applicants: University of Maryland, College Park, College Park, MD (US); Aerosol Dynamics, Inc., Berkeley, CA (US)

(72) Inventors: Donald K. Milton, University Park, MD (US); Somayeh Youssefi, Hyattsville, MD (US); Susanne V. Hering, Berkely, CA (US); Gregory S. Lewis, Berkeley, CA (US)

(73) Assignees: University of Maryland, College Park, College Park, MD (US); Aerosol Dynamics, Inc., Berkeley, CA (US)

( * ) Notice: Subject to any disclaimer, the term of this patent is extended or adjusted under 35 U.S.C. 154(b) by 196 days.

(21) Appl. No.: 15/490,591

(22) Filed: Apr. 18, 2017

(65) Prior Publication Data

US 2017/0299477 A1 Oct. 19, 2017

Related U.S. Application Data

(60) Provisional application No. 62/324,254, filed on Apr. 18, 2016.

(51) Int. Cl.
*G01N 1/22* (2006.01)
*G01N 1/42* (2006.01)
(Continued)

(52) U.S. Cl.
CPC .......... *G01N 1/2208* (2013.01); *A61B 5/082* (2013.01); *A61B 5/097* (2013.01); *G01N 1/42* (2013.01);
(Continued)

(58) Field of Classification Search
CPC .......... G01N 1/2208; G01N 1/42; G01N 1/22; G01N 33/497; G01N 2001/2244;
(Continued)

(56) References Cited

U.S. PATENT DOCUMENTS 4,250,890 A 2/1981 Jones et al.
6,363,772 B1 4/2002 Berry
(Continued)

FOREIGN PATENT DOCUMENTS

CN 103328951 4/2017
DE 102007012210 3/2007
(Continued)

OTHER PUBLICATIONS

Adler M et al. (2003) "*A real-time immuno-PCR assay for routine ultrasensitive quantification of proteins*," Biochem. Biophys. Res. Commun. 308:240-50.
(Continued)

*Primary Examiner* — Nathaniel J Kolb
(74) *Attorney, Agent, or Firm* — William C. Schrot; AuerbachSchrot LLC

(57) ABSTRACT

The present invention relates to systems and methods for collecting and analyzing bioaerosols, including exhaled breath aerosol from a subject. The collection system comprises an inlet portion configured to receive a gaseous fluid containing water vapor and aerosol particles. A primary passage for gaseous fluid flow is in fluid communication with the inlet portion and configured to channel the gaseous fluid flow therethrough. An outlet portion is in fluid communication with the primary passage. A sample collection region is provided, which is configured to receive from the outlet portion aerosol particles from the gaseous fluid, wherein the aerosol particles are impacted onto a layer of ice.

30 Claims, 7 Drawing Sheets

US 10,502,665 B2

Page 2

(51) Int. Cl.
*G01N 33/497* (2006.01)
*A61B 5/097* (2006.01)
*A61B 5/08* (2006.01)
*G01N 15/00* (2006.01)

(52) U.S. Cl.
CPC ... *G01N 33/497* (2013.01); *G01N 2001/2223* (2013.01); *G01N 2001/2244* (2013.01); *G01N 2001/2282* (2013.01); *G01N 2015/0026* (2013.01); *G01N 2033/4975* (2013.01)

(58) Field of Classification Search
CPC ... G01N 2001/2223; G01N 2001/2282; G01N 2033/4975; A61B 5/082; A61B 5/097
See application file for complete search history.

(56) References Cited

U.S. PATENT DOCUMENTS

| | | | |
|---|---|---|---|
| 6,609,068 | B2 | 8/2003 | Cranley et al. |
| 6,712,881 | B2 | 3/2004 | Hering et al. |
| 7,118,537 | B2 | 10/2006 | Baddour |
| 7,153,272 | B2 | 12/2006 | Talton |
| 7,241,989 | B2 | 6/2007 | Miller et al. |
| 7,297,120 | B2 | 11/2007 | Tsukashima et al. |
| 7,347,825 | B2 | 3/2008 | Vaughan et al. |
| 7,364,553 | B2 | 4/2008 | Paz et al. |
| 7,380,550 | B2 | 6/2008 | Sexton et al. |
| 7,547,285 | B2 | 6/2009 | Kline |
| 7,736,421 | B2 | 6/2010 | Hering et al. |
| 7,819,803 | B2 | 10/2010 | Burch et al. |
| 7,972,277 | B2 | 7/2011 | Oki et al. |
| 7,992,422 | B2 | 8/2011 | Leddy et al. |
| 8,028,775 | B2 | 10/2011 | Orenbuch |
| 8,250,903 | B2 | 8/2012 | McDevitt et al. |
| 8,316,852 | B2 | 11/2012 | Pouteau et al. |
| 8,368,883 | B2 | 2/2013 | Palmskog et al. |
| 8,459,752 | B2 | 6/2013 | Russell |
| 8,491,494 | B2 | 7/2013 | Kline et al. |
| 8,627,821 | B2 | 1/2014 | Edwards et al. |
| 8,705,029 | B2 | 4/2014 | Palmskog et al. |
| 8,801,838 | B2 | 8/2014 | Hering et al. |
| 9,028,775 | B2 | 5/2015 | Lewis et al. |
| 9,395,281 | B2 | 7/2016 | Wang et al. |
| 9,579,662 | B2 | 2/2017 | Hering et al. |
| 9,610,531 | B2 | 4/2017 | Hering et al. |
| 9,976,944 | B2 | 5/2018 | Olin et al. |
| 2004/0016680 | A1* | 1/2004 | Call ........ B01D 45/08 209/1 |
| 2007/0053842 | A1 | 8/2007 | Okpala |
| 2007/0203424 | A1* | 8/2007 | Kline ........ A61B 5/097 600/543 |
| 2008/0214947 | A1 | 9/2008 | Hunt et al. |
| 2009/0269767 | A1 | 10/2009 | Soderlund et al. |
| 2010/0087749 | A1 | 4/2010 | Tovey |
| 2010/0242633 | A1 | 9/2010 | McDevitt et al. |
| 2010/0297635 | A1 | 11/2010 | Olin et al. |
| 2010/0324439 | A1 | 12/2010 | Davenport |
| 2012/0131989 | A1* | 5/2012 | Vanhanen ........ G01N 15/06 73/28.01 |
| 2012/0212735 | A1 | 8/2012 | Palmskog et al. |
| 2014/0288454 | A1 | 9/2014 | Paz et al. |

FOREIGN PATENT DOCUMENTS

| | | |
|---|---|---|
| DE | 10392241 | 3/2009 |
| EP | 2108456 | 10/2009 |
| EP | 2361387 | 3/2011 |
| JP | 5908475 | 4/2016 |
| WO | WO 2007120644 | 10/2007 |
| WO | WO 2008/106961 | 9/2008 |
| WO | WO 2011/029888 | 3/2011 |
| WO | WO 2013/061091 | 5/2013 |
| WO | WO 2015/015201 | 2/2015 |

OTHER PUBLICATIONS

Adler M et al. (2008) "*Sensitivity by combination: immuno-PCR and related technologies*," Analyst 133:702-718.

Alberg AJ and Samet JM (2003) "*Epidemiology of lung cancer*," Chest. 123:21S-49S.

Almstrand A et al. (2010) "*Effect of airway opening on production of exhaled particles*," J. Appl. Physiol. 108:584-8.

Almstrand AC et al. (2009) "*Airway monitoring by collection and mass spectrometric analysis of exhaled particles*," Anal. Chem. 81:662-668.

Almstrand AC et al. (2012) "*TOF-SIMS analysis of exhaled particles from patients with asthma and healthy controls*," Eur. Respir. J. pp. 59-66.

Aziz N et al. (1999) "*Variables that affect assays for plasma cytokines and soluble activation markers*," Clin. Diagn. Lab Immunol. 6: 89-95.

Barletta J et al. (2009) "*Immunomagnetic quantitative immuno-PCR for detection of less than one HIV-1 virion*," J. Virol. Methods 157:122-32.

Barletta JM et al. (2005) "*Detection of ultra-low levels of pathologic prion protein in scrapie infected hamster brain homogenates using real-time immuno-PCR*," J. Virol. Methods 127:154-64.

Bayley DL et al. (2008) "*Validation of assays for inflammatory mediators in exhaled breath condensate*," Eur. Respir. J. 31:943-948.

Bredberg, A. et al. (2012) "*Exhaled endogenous particles contain lung proteins*," Clin. Chem. 58(2):431-440.

Broding HC et al. (2009) "*Comparison between exhaled breath condensate analysis as a marker for cobalt and tungsten exposure and biomonitoring in workers of a hard metal alloy processing plant*," Int. Arch. Occup. Environ. Health. 82:565-573.

Burbulis I et al. (2005) "*Using protein-DNA chimeras to detect and count small numbers of molecules*," Nat. Methods 2:31-7.

Burbulis I et al. (2007) "*Quantifying small numbers of antibodies with a near-universal protein-DNA chimera*," Nat. Methods 4:1011-3.

Carpagnano GE et al. (2002) "*Interleukin-6 is increased in breath condensate of patients with non-small cell lung cancer*," Int. J. Biol. Markers, 17:141 (Abstract).

Cikach, FS and Dweik, RA (2012) "*Cardiovascular Biomarkers in Exhaled Breath*," Prog. Cardiovasc. Dis. 55(1):34-43.

DeMore JP et al. (2009) "*Similar colds in subjects with allergic asthma and nonatopic subjects after inoculation with rhinovirus-16*," J. Allergy Clin. Immunol. 124:245-252.

Doherty DE (2008) "*A review of the role of FEV1 in the COPD paradigm*," COPD 5: 310-318.

Drummond GB and Milic-Emili J (2007) "*Forty years of closing volume*," Br. J. Anaesth. 99:772-4.

Edwards DA et al. (2004) "*Inhaling to mitigate exhaled bioaerosols*," Proc. Natl. Acad. Sci. USA 101:17383-17388.

Effros RM et al. (2002) "*Dilution of respiratory solutes in exhaled condensates*," Am. J. Respir. Crit. Care Med. 165:663-669.

Effros RM et al. (2005) "*Epithelial lining fluid solute concentrations in chronic obstructive lung disease patients and normal subjects*," J. Appl. Physiol. 99:1286-1292.

Fabian P et al. (2008) "*Influenza virus in human exhaled breath: an observational study*," PLoS One 3:e2691(16 pages).

Fabian P et al. (2009) "*Airborne influenza virus detection with four aerosol samplers using molecular and infectivity assays: considerations for a new infectious virus aerosol sampler*," Indoor Air 19:433-441.

Fabian P et al. (2009) "*An optimized method to detect influenza virus and human rhinovirus from exhaled breath and the airborne environment*," J. Envir. Monitoring 11:314-7.

Fabian P et al. (2011) "*Origin of exhaled breath particles from healthy and human rhinovirus-infected subjects*," J. Aerosol. Med. Pulm. Drug Deliv. 24:137-147.

Fairchild CI and Stampfer JF (1987) "*Particle concentration in exhaled breath*," Am. Ind. Hyg. Assoc. J. 48:948-949.

Fennelly KP et al. (2004) "*Cough-generated aerosols of Mycobacterium tuberculosis: a new method to study infectiousness*," Am. J. Respir. Crit. Care Med. 169:604-609.

(56) References Cited

OTHER PUBLICATIONS

Garey KW et al. (2004) "Markers of inflammation in exhaled breath condensate of young healthy smokers," Chest. 125: 22-26.

Goldoni M et al. (2008) "Chromium in exhaled breath condensate and pulmonary tissue of non-small cell lung cancer patients," Int. Arch. Occup. Environ. Health, 81:487-493.

Han T et al. (2010) "Performance of an Electrostatic Precipitator with Superhydrophobic Surface when Collecting Airborne Bacteria," Aerosol Sci. Technol. 44:339-348.

Hering, SV et 1. (2014) "*Moderated, Water-Based, Condensational Particle Growth in Laminar Flow*," Aerosol Sci. And Technol. 48(4):401-408.
Holmgren H et al. (2010) "*Size distribution of exhaled particles in the range from 0.01 to 2.0 mu m*," J. Aerosol Sci. 41:439-46.
Horvath I et al. (2005) "*Exhaled breath condensate: methodological recommendations and unresolved questions*," Eur. Respir. J. 26:523-48.
Horvath I et al. (2009) "*Exhaled biomarkers in lung cancer*," Eur. Respir. J. 34:261-275.
Houseman EA et al. (2006) "*A nonstationary negative binomial time series with time-dependent covariates: Enterococcus counts in Boston Harbor*," J. Am. Stat. Assoc. 101:1365-1376.
Hunt J (2007) "*Exhaled Breath Condensate—an overview*," Immunol Allergy Clin. North Am. 27(4):587.
Huynh KN et al. (2008) "*A new method for sampling and detection of exhaled respiratory virus aerosols*," Clin. Infect. Dis. 46:93-95.
Johnson GR and Morawska L (2009) "*The mechanism of breath aerosol formation*," J. Aerosol Med. Pulm. Drug Deliv. 22:229-237.
Kazani S and Israel E (2010) "*Exhaled breath condensates in asthma: diagnostic and therapeutic implications*," J. Breath Res. 4:047001.
Kietzmann D et al. (1993) "*Hydrogen peroxide in expired breath condensate of patients with acute respiratory failure and with ARDS*," Intensive Care Med. 19:78-81.
King M et al. (1985) "*Clearance of mucus by simulated cough*," J. Appl. Physiol. 58:1776-1782.
Larsson P et al. (2012) "*Surfactant protein A and albumin in particles in exhaled air*," Respir. Med. 106:197-204.
Leung TF et al. (2004) "*Increased macrophage-derived chemokine in exhaled breath condensate and plasma from children with asthma*," Clin Exp Allergy, 34:786-791.
Liu J and Thomas PS (2007) "*Relationship between exhaled breath condensate volume and measurements of lung volumes*," Respiration 74:142-145.
Liu Y and Daum PH (2000) "*The effect of refractive index on size distributions and light scattering coefficients derived from optical particle counters*," J. Aerosol. Sci. 31:945-957.
Loukides S et al. (2011) "*Exhaled breath condensate in asthma: from bench to bedside*," Curr. Med. Chem. 18:1432-1443.
MacDowell AL and Bacharier LB (2005) "*Infectious triggers of asthma*," Immunol. Allergy Clin. North Am. 25:45-66.
Mainelis G et al. (2002) "*Design and Collection Efficiency of a New Electrostatic Precipitator for Bioaerosol Collection*," Aerosol Sci. Technol. 36:1073-1085.
Mannino DM and Braman S (2007) "*The epidemiology and economics of chronic obstructive pulmonary disease*," Proc. Am. Thorac. Soc. 4: 502-506.
Markey AL et al. (2010) "*High-throughput droplet PCR*," Methods 50:277-81.
Martinez et al. (2004) "*Exposure assessment and analysis for biological agents*," Grana, 43(4):193-208.
McKenzie et al. (2012) "*Collection of Aerosolized Human Cytokines Using Teflon Filters*," Plos One 7:e35814 (11 pages).
McKenzie JH (2010) "*Methods for environmental endotoxin assay and respiratory biomarker measurement*," Lowell, MA: University of Massachusetts Lowell, School of Health & Environment.
McKenzie JH et al. (2009) "*Use of Teflon filters improves collection efficiency of aerosolized cytokines*," Am. J. Respir. Crit. Care Med. 179:A1365.
Montuschi (2007) "*Analysis of exhaled breath condensate in respiratory medicine; methodological aspects and potential clinical applications*," Therapeutic Advances in Respiratory Disease, 1(1):5-23.
Morawska L et al. (2009) "*Size distribution and sites of origin of droplets expelled from the human respiratory tract during expiratory activities*," J. Aerosol. Sci. 40:256-269.
Moriarty JA and Grotberg JB (1999) "*Flow-induced instabilities of a mucus-serous bilayer*," J. Fluid Mech. 397:1-22.
Muccilli, V. et al. (2015) "*Protein profile of exhaled breath condensate determined by high resolution mass spectrometry*," J. Phann Biomed. Anal., 105:134-149.
Mutti A et al. (2006) "*Exhaled metallic elements and serum pneumoproteins in asymptomatic smokers and patients with COPD or asthma*," Chest. 129:1288-1297.
Nicas M et al. (2005) "*Toward understanding the risk of secondary airborne infection: emission of respirable pathogens*," J. Occup. Environ. Hyg. 2: 143-154.
Niemeyer CM et al. (2005) "*Immuno-PCR: high sensitivity detection of proteins by nucleic acid amplification*," Trends Biotechno. 23:208-216.
Niemeyer CM et al. (2007) "*Detecting antigens by quantitative immuno-PCR*," Nat. Protoc. 2:1918-930.
Ottesen EA et al. (2006) "*Microfluidic digital PCR enables multigene analysis of individual environmental bacteria*," Science 314:1464-7.
Panicker G et al. (2007) "*Effect of storage temperatures on the stability of cytokines in cervical mucous*," Cytokine 37:176-179.
Papineni RS and Rosenthal FS (1997) "*The size distribution of droplets in the exhaled breath of healthy human subjects*," J. Aerosol Med. 10:105-16.
Pinnick RG et al. (2000) "*Response Characteristics of the Particle Measuring Systems Active Scattering Aerosol Spectrometer Probes*," London: Taylor & Francis, pp. 334-352.
Pitkaranta A and Hayden FG (1998) "*Rhinoviruses: important respiratory pathogens*," Ann. Med. 30:529-537.
Rajkovic A. (2006) "*Immunoquantitative real-time PCR for detection and quantification of Staphylococcus aureus Enterotoxin B in foods*," Appl. Environ. Microbiol., 72:6593-6599.
Rennard SI (1998) "*COPD: overview of definitions, epidemiology, and factors influencing its development*," Chest. 113:235S-241S.
Rosias P et al. (2004) "*Childhood asthma: exhaled markers of airway inflammation, asthma control score, and lung function tests*," Pediatr. Pulmonol. 38:107-114.
Rosias P et al. (2004) "*Exhaled breath condensate: a space odessey, where no one has gone before*," Eur. Respir. J. 24:189-190.
Rudnick SN and Milton DK (2003) "*Risk of indoor airborne infection transmission estimated from carbon dioxide concentration*," Indoor Air. 13:237-245.
Sack U et al. (2006) "*Multiplex analysis of cytokines in exhaled breath condensate*," Cytometry A. 69:169-72.
Sapey E et al. (2008) "*The validation of assays used to measure biomarkers in exhaled breath condensate*," Eur. Respir. J. 32:1408-1409.
Schaerli Y et al. (2009) "*Continuous-flow polymerase chain reaction of single-copy DNA in microfluidic microdroplets*," Anal. Chem. 81:302-6.
Scheideler, L et al. (1993) "*Detection of nonvolatile macromolecules in breath. A possible diagnostic tool?*" Am. Rev. Respir. Dis. 148:778 (Abstract).
Schwarz K et al. (2010) "*Characterization of exhaled particles from the healthy human lung—a systematic analysis in relation to pulmonary function variables*," J. Aerosol Med. Pulm. Drug Deliv. 23:371-9.
Shahid SK et al. (2002) "*Increased interleukin-4 and decreased interferon-gamma in exhaled breath condensate of children with asthma*," Am. J. Respir. Crit. Care Med., 165:1290-1293.
Shevchenko, A. et al. (2006) "*In-gel digestion for mass spectrometric characterization of proteins and proteomes*," Nat. Protoc. 1(6):2856-2860.
Srisa-Art M et al. (2009) "*High-throughput confinement and detection of single DNA molecules in aqueous microdroplets*," Chem. Commun. (Cam b) 6548-50.

(56) References Cited

OTHER PUBLICATIONS

Stanley WM (1944) "*The size of influenza virus*," J. Exp. Med. 79:267-283.
Thavasu PW et al. (1992) "*Measuring cytokine levels in blood. Importance of anticoagulants, processing, and storage conditions*," J. Immunol. Methods 153:115-124.
Urbano FL (2008) "*Review of the NAEPP 2007 Expert Panel Report (EPR-3) on Asthma Diagnosis and Treatment Guidelines*," J. Manag. Care Pharm. 14: 41-49.
Verreault D et al. (2008) "*Methods for sampling of airborne viruses*," Microbiol. Mol. Biol. Rev. 72:413-444.
Wang F and Burns MA (2009) "*Performance of nanoliter-sized droplet-based microfluidic PCR*," Biomed. Microdevices (10 pages).
Weist S et al. (2010) "*Effects of thawing, refreezing and storage conditions of tissue samples and protein extracts on 2-DE spot intensity*," Proteomics 10:1515-1521.
Wisnewski, A.V. et al. (2000) "*Identification of human lung and skin proteins conjugated with hexamethylene diisocyanate in vitro and in vivo*," Am. J. Respir. Crit. Care Med., 162(6):2330 (Abstract).
Wood SN (2000) "*Modeling and smoothing parameter estimation with multiple quadratic penalties*," J. Stat. Soc. (B) 62:413-428.
Eiguren et al. (2014) "*Design and Laboratory Evaluation of a Sequential Spot Sampler for Time-Resolv1—d Measurement of Airborne Particle Composition*" Aerosol Science and Technology, 48:655-663.
Eiguren-Fernandez et al. (2017) "*An online monitor of the oxidative capacity of aerosols (o-MOCA)*" Atmospheric Measurement Techniques, 10(2):633-644.
Eiguren-Fernandez et al. (2014) "*Time-resolved characterization of particle associated polycyclic aromatic hydrocarbons using a newly-developed sequential spot sampler with automated extraction and analysis*" Atmospheric Environment, 96: 125-134.
Hecobian et al. (2016) "*Evaluation of the Sequential Spot Sampler (S3) for time-resolved measurement of PM 2.5 sulfate and nitrate through lab and field measurements*. Atmospheric Measurement Techniques" 9(2): 525-533.
Hering et al. (2014) "*Moderated, water-based condensational growth of particles in a laminar flow*" Aerosol Science and Technology, 48:401-40.
Hering et al. (2005) "*A laminar-flow, water-based condensation particle cour 1 ter (WCPC)*" Aerosol Science and Technology, 39 (7): 659-672.
Hering et al. (2005) "*A method for particle size amplification by water condensation in a laminar, thermally diffusive flow*" Aerosol Science and Technology, 39 (5): 428-436.
Hering et al. (2017) "Detection near 1-nm with a laminar-flow, water-based condensation particle counter "Aerosoln Science and Technology, 51(3): 354-362.
Iida et al. (2008) "*An ultrafine water-based condensation particle counter and its evaluation under field conditions*" Aerosol Science and Technology 42(10) 862-871.
Jiang et al. (2016) "*Use of RNA Amplification and Electrophoresis for Studying Virus Aerosol Collection Efficiency and Their Comparison with Plaque Assays*" Electrophoresis, 37(19): 2574-2580.
Kangasluoma et al. (2017) "*Characterization of three new condensation particle counters for sub-3 nm particle detection during the Helsinki CPC workshop: the ADI versatile water CPC, TSI 3777 Nano enhancer and boosted TSI 3010*." Atmospheric Measurement Techniques, 10(6): 2271-2281.
Lednicky et al . (2016) "*Highly efficient collection of infectious pandemic influenza H1N1 virus (2009) through laminarllow water based condensation*" Aerosol Science and Technology, 50(7):i-iv.
Lewis et al. (2013) "*Minimizing concentration effects in water-based, laminar-flow condensation particle counters*" Aerosol Science and Technology, 47(6): 645-654.
Noblitt et al. (2009) "*Interfacing Microchip Elecfrophoresis to a Growth Tube Particle Collector for Semicontinuous Monitoring of Aerosol Composition*" Analytical Chemistry 81 (24):10029-10037.
Noblitt et atl. (2009) "*High-sensitivity microchip electrophoresis determination of inorganic anions and oxalate in atmospheric aerosols with adjustable selectivity and conductivity detection*" Journal of.Chromatography A, 1216 (9) 1503-1510.
Pan et al. (2016) "*Efficient Collection of Viable Virus Aerosol through Laminar-Flow, Water-Based Condensational Particle Growth*" Journal of applied microbiology. 120(3): 805-815.
Pan, Maohua et al. (2017) "*Collection of Viable Aerosolized Influenza Virus and Other Respiratory Viruses in a Student Health Care Center through Water-Based Condensation Growth*" mSphere 2(5): e00251-17.
Pinterich et al. (2017) "*A Water-based Fast Integrated Mobility Spectrometer (WFIMS) with enhanced dynamic size range*" Aerosol Science and Technology, 51(10): 1212-1222.
Pinterich et al. (2017) "*A Humidity-controlled Fast Integrated Mobility Spectrometer* (HFIMS) *for rapid measurements of particle hygroscopic growth*" Atmospheric Measurement Techniques, 10(12): 4915-4925.
Spielman et al. (2017) "*Preliminary Investigation of a Water-based Method for Fast Integrating Mobility Spectrometry*" Aerosol Science and Technology, 51(10): 1223-1230.
Walls et al. (2016) "*Generation and sampling of nanoscale infectious viral aerosols*" Aerosol Science and Technology, 50(8): 802-811.
Walls et al. (2017) "*Long-term viable bioaerosol sampling using a temperature-and humidity-controlled filtration apparatus, a laboratory investigation using culturable E. coli.*" Aerosol Science and Technology, 51(5): 576-586.
Antus, B., et al. (2010) "*Analysis of Cytokine Pattern in Exhaled Breath Condensate of Lung Transplant Recipients with Bronchiolitis Obliterans Syndrome*," Inflamm Res. 59: 83-86.
Bondi, Z.L., et al. (2007) "*Variability of Exhaled Breath Condensate Leukotriene $B_4$ and 8-isoprostane in COPD Patients*," Int'l J. COPD 2(1): 71-76.
Gebhart, J., et al. (1988) "*The Human Lung as Aerosol Particle Generator*," J. Aerosol Med. 1: 196-197.
Horváth, I., et al. (2001) "'*Haemoxygenase-1 Induction and Exhaled Markers of Oxidative Stress in Lung Diseases', Summary of the ERS Research Seminar in Budapest, Hungary, Sep. 1999*," Eur. Respir. J. 18: 420-430.
Horváth, I., et al. (2017) "*A European Respiratory Society Technical Standard: Exhaled Biomarkers in Lung Disease*," Eur. Respir. J. 49: 1600965 (pp. 1-26).
Lärstad, M., et al. (2015) "*Surfactant Protein a in Exhaled Endogenous Particles is Decreased in Chronic Obstructive Pulmonary Disease (COPD) Patients: A Pilot Study*," PLoS One 10(12): e0144463 (pp. 1-14).
Lin, X., et al. (2017) "*Correlation Analysis of Surfactant Protein A and Surfactant Protein D with Lung Function in Exhaled Breath Condensate from Lung Cancer Patients with and without COPD*," Molecular Med. Rep. 16: 4948-4954.
Ljungkvist, G., et al. (2018) "*Two Techniques to Sample Non-Volatiles in Breath—Exemplified by Methadone*," J. Breath Res. 12: 016011 (pp. 1-9).
Olin, A.C., et al. (2015) "*Surfactant Protein A in Particles in Exhaled Air is Decreased in Lung Transplant Patients Before Diagnosis of Chronic Rejection*," Am. J. Respir. Crit. Care Med. 191: A6138 (Abstract Only).
Silkoff, P.E., et al. (2006) "*ATS Workshop Proceedings: Exhaled Nitric Oxide and Nitric Oxide Oxidative Metabolism in Exhaled Breath Condensate*," Proc. Am. Thorac. Soc. 3: 131-145.
Zamuruyev, K.O., et al. (2017) "*Human Breath Metabolomics Using an Optimized Non Invasive Exhaled Breath Condensate Sampler*," J. Breath Res. 11: 016001 (pp. 1-14).

* cited by examiner

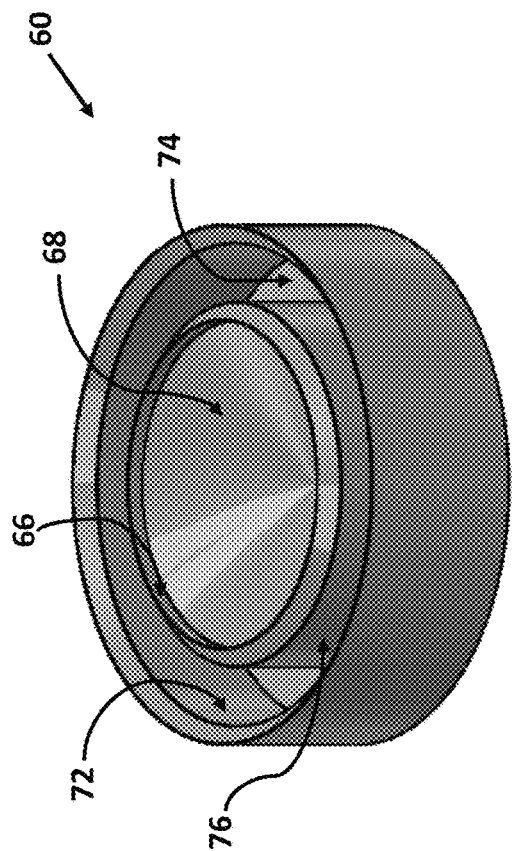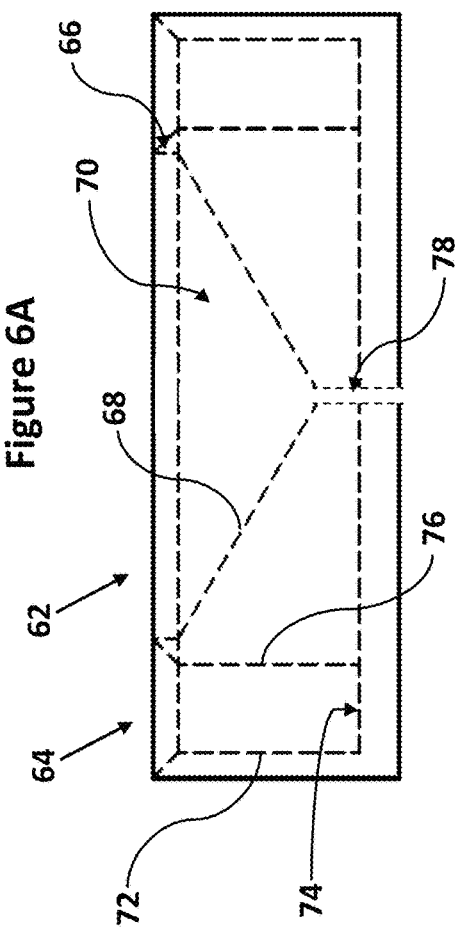

AEROSOL COLLECTION SYSTEM AND METHOD

STATEMENT REGARDING FEDERALLY SPONSORED RESEARCH OR DEVELOPMENT

This invention was made with government support by the Office of the Director of National Intelligence (ODNI), Intelligence Advanced Research Projects Activity (IARPA), via the Federal Bureau of Investigation under DJF-15-1200-K-0001725. The United States government has certain rights in this invention.

CROSS-REFERENCE TO RELATED APPLICATIONS

This application is based on U.S. Provisional Patent Application Ser. No. 62/324,254, filed Apr. 18, 2016, titled "Advanced Exhaled Breath Aerosol (EBA) and General Bioaerosol Collection for Infectious Agents & Biomarker Detection Using Cryogenic Impaction," which application is incorporated herein by reference in its entirety and to which priority is claimed.

FIELD OF THE INVENTION

The present invention relates to systems and methods for collecting aerosol particles from a gaseous fluid, and in particular exhaled breath aerosol from exhaled breath from a subject.

BACKGROUND OF THE INVENTION

Exhaled breath from an individual contains thousands of molecules that can provide useful information about the individual's health. Breath analysis therefore has the potential to provide relatively inexpensive, rapid, noninvasive methods for detecting and/or monitoring a variety of metabolic processes and diseases. Breath analysis also provides utility in other applications, such as environmental monitoring, security, etc. (Cikach, F S and Dweik, R A (2012) "*Cardiovascular Biomarkers in Exhaled Breath*," Prog. Cardiovasc. Dis. 55(1):34-43).

Exhaled breath contains mostly water vapor, as well as smaller amounts of volatile, semi-volatile, and non-volatile particles derived from the upper and lower portions of the respiratory system (Effros, R M et al. (2005) "*Epithelial lining fluid solute concentrations in chronic obstructive lung disease patients and normal subjects*," J. Appl. Physiol. 99:1286-1292; Horvath, I et al. (2005) "*Exhaled breath condensate: methodological recommendations and unresolved questions*," Eur. Respir. J. 26:523-548; McKenzie, J H et al. (2012) "*Collection of Aerosolized Human Cytokines Using Teflon® Filters*," PLoS ONE, vol. 7, issue 5, page 1-11, e35814). It has been shown that approximately 98% of the particles produced during tidal breathing are under 1 μm (Fairchild, C I and Stampfer, J F (1987) "*Particle concentration in exhaled breath*," Am. Ind. Hyg. Assoc. J. 48:948-949; Papineni, R S and Rosenthal, F S (1997) "*The size distribution of droplets in the exhaled breath of healthy human subjects*," J. Aerosol Med. 10:105-116; Edwards, D A et al. (2004) "*Inhaling to mitigate exhaled bioaerosols*," Proc. Natl. Acad. Sci. USA 101:17383-17388; Morawska, L et al. (2008) "*Size distribution and sites of origin of droplets expelled from the human respiratory tract during expiratory activities*," J. Aerosol. Sci. 40:256-269). For example, in a previous study of subjects infected with influenza, it was found that the subjects produced 67 to 8500 particles per liter of air, and that 87% of the particles were under 1 μm (Fabian, P et al. (2008) "*Influenza virus inhuman exhaled breath: an observational study*," PLoS ONE 3:e2691).

Numerous volatile organic compounds (VOCs) have been identified in exhaled human breath, some of which have been associated with metabolic pathways and processes (see Cikach, F. S. & Dweik, R. A. (2012), supra, Prog. Cardiovasc. Dis. 55(1):34-43). However, far fewer studies have been conducted on non-volatile compounds in exhaled breath. Non-volatile substances incorporated in aerosolized particles are believed to derive from the respiratory tract lining fluid (RTLF), which is a heterogeneous lining layer that covers the respiratory epithelium (Scheideler, L et al. (1993) "*Detection of nonvolatile macromolecules in breath. A possible diagnostic tool?*" Am. Rev. Respir. Dis. 148:778). In the upper airways (from the trachea to the approximately the $15^{th}$ generation of airway divisions), the RTLF includes a gel layer over a sol layer. It contains high levels of mucins, secreted by goblet cells and submucosal mucus gland mucous cells. Lipids, lipid metabolites, proteoglycans, proteases and antimicrobial proteins and peptides are also constituents of the RTLF in the upper airways. Alveoli begin to appear at about the $15^{th}$ generation of airway divisions and are more frequent until at about the $23^{rd}$ division the airways terminate in alveolar sacks. The alveolar epithelium is very thin, and coated with surfactant, a complex mixture comprised of glycerophospholipids (~80%), neutral lipids (~10%), and proteins (~10%). (Levitzky, M. G. (2013). Chapter 1. Function and Structure of the Respiratory System. In Pulmonary Physiology, (New York, N.Y.: The McGraw-Hill Companies); Widdicombe, J. (2012). Airway Epithelium. Colloquium Series on Integrated Systems Physiology: From Molecule to Function 4, 1-148).

It has long been thought that during tidal breathing, exhaled aerosol particles (e.g., droplets of RTLF) are generated by shear forces produced by air flow acting on the airway lining fluid, thereby entraining particles composed of mucus, surfactant and pathogens (King, M et al. (1985) "*Clearance of mucus by simulated cough*," J. Appl. Physiol. 58:1776-1782; Moriarty, J A and Grotberg, J B (1999) "*Flow-induced instabilities of a mucus-serous bilayer*," J. Fluid Mech. 397:1-22; see also Leith, D et al. (1986) "*Cough*" in M J Macklem (ed). Handbook of Physiology, The Respiratory System, Section 3, Vol. III, Part 1, Bethesda, Md.: American Physiological Society, pp. 315-336). However, more recent evidence has strongly supported the hypothesis that RTLF droplets are produced from the destabilization of the lining fluid during the reopening of collapsed small airways and alveoli during breathing (Edwards, D A et al. (2004), supra., Proc. Natl. Acad. Sci. USA 101:17383-17388; see also Johnson, G R and Morawska, L (2009) "*The mechanism of breath aerosol formation*," J. Aerosol Med. Pulm. Drug Deliv. 22:229-237). Identifying the origin of these particles is important when interpreting studies of exhaled breath biomarkers (Shahid, S K et al. (2002) "*Increased interleukin-4 and decreased interferon-gamma in exhaled breath condensate of children with asthma*," Am. J. Respir. Crit. Care Med., 165:1290-1293; Garey, K W et al. (2004) "*Markers of inflammation in exhaled breath condensate of young healthy smokers*," Chest. 125: 22-26; Rosias, P P et al. (2004) "*Childhood asthma: exhaled markers of airway inflammation, asthma control score, and lung function tests*," Pediatr. Pulmonol. 38:107-114; Carpagnano, G E et al. (2002) "*Interleukin-6 is increased in breath condensate of patients with non-small cell lung cancer*," Int. J. Biol. Markers, 17:141-145; Leung, T F et al. (2004) "*Increased macrophage-derived chemokine in exhaled breath condensate and plasma from children with asthma*," Clin Exp Allergy, 34:786-791; and Rosias, P et al. (2004) "*Exhaled breath condensate: a space odessey, where no one has gone before*," Eur. Respir. J. 24:189-190), metals in exhaled breath (Broding, H C et al. (2009) "*Comparison between exhaled breath condensate analysis as a marker for cobalt and tungsten exposure and biomonitoring in workers of a hard metal alloy processing plant*," Int. Arch. Occup. Environ. Health. 82:565-573; Goldoni, M et al. (2008) "*Chromium in exhaled breath condensate and pulmonary tissue of non-small cell lung cancer patients*," Int. Arch. Occup. Environ. Health, 81:487-493; Mutti, A et al. (2006) "*Exhaled metallic elements and serum pneumoproteins in asymptomatic smokers and patients with COPD or asthma*," Chest. 129:1288-1297), pathogens such as viruses (Fabian, P et al. (2008), supra., PLoS ONE 3:e2691; Huynh, K N et al. (2008) "*A new method for sampling and detection of exhaled respiratory virus aerosols*," Clin. Infect. Dis. 46:93-95) and bacteria (Fennelly, K P et al. (2004) "*Cough-generated aerosols of Mycobacterium tuberculosis: a new method to study infectiousness*," Am. J. Respir. Crit. Care Med. 169:604-609).

Thus, there has been great interest in noninvasive techniques for the collection and analysis of biomarkers present in aerosolized particles. The availability of sampling methods that are convenient for the patient and can be performed on a regular basis would greatly facilitate the early detection of airway disease and the monitoring of disease progression and the patient's response to therapy. Moreover, non-invasive methods are unlikely to harm the airways during sampling.

Conventional techniques for obtaining samples containing biomarkers from exhaled breath have primarily focused on the collection of exhaled breath condensate (EBC). EBC samples include a mixture of three main components (Horvath, I et al. (2005), supra., Eur. Respir. J. 26:523-548). The most abundant component of EBC samples is liquid water (>99%) formed from the condensation of water vapor present in the warm exhaled air, saturated with water vapor as it leaves the respiratory tract. The second and third components of EBC samples are water-soluble volatile and non-volatile droplets that are aerosolized from the RTLF and are present in significantly smaller amounts than the water vapor component (Horvath, I et al. (2005), supra., Eur. Respir. J. 26:523-548; Kietzmann, D et al. (1993) "*Hydrogen peroxide in expired breath condensate of patients with acute respiratory failure and with ARDS*," Intensive Care Med. 19:78-81; Effros, R M et al. (2002) "*Dilution of respiratory solutes in exhaled condensates*," Am. J. Respir. Crit. Care Med. 165:663-669; Horvath, I et al. (2009) "*Exhaled biomarkers in lung cancer*," Eur. Respir. J. 34:261-275; Kazani, S and Israel, E (2010) "*Exhaled breath condensates in asthma: diagnostic and therapeutic implications*," J. Breath Res. 4:047001; Loukides, S et al. (2011) "*Exhaled breath condensate in asthma: from bench to bedside*," Curr. Med. Chem. 18:1432-1443; McKenzie, J H et al. (2012), supra, PLoS ONE, vol. 7, issue 5, page 1-11, e35814).

Collection of EBC samples is typically accomplished through means whereby a subject breathes tidally into a chilled collection device for a fixed period of time (e.g., 10 minutes). The exhaled breath is then condensed in the device, and as much of the resulting condensate as possible is collected. Unfortunately, the significant amount of liquid water from condensed water vapor present in EBC samples dilutes the inherently low concentrations of certain analytes, particularly non-volatile biomarkers from RTLF droplets, to levels that are at or below the detection threshold of most conventional assays. For example, analyte concentrations may be diluted by 20000-fold or more by the condensed liquid water using conventional EBC collection systems. Moreover, inefficient collection of aerosolized droplets of RTLF results in substantial sample loss. EBC devices collect aerosol particles, including droplets of RTLF, by allowing turbulence to result in impaction on the walls of the device. However, variable airflow rates during exhalation result in variable turbulence and impaction. For example, the aerosol particle collection efficiency of most conventional EBC devices is less than 25%. Some EBC collection methods also provide for efficient impaction of collected EBC into a liquid medium, but, thereby also diluting analyte concentrations (see U.S. Pat. No. 9,617,582).

The inefficient collection of exhaled, RTLF droplets containing non-volatile aerosol particles and the extensive collection of water vapor using conventional EBC collection methods, combined with most assay sensitivity limitations, has therefore created significant problems with reproducibility and validity of biomarker measurements (Horvath, I et al. (2005), supra., Eur. Respir. J. 26:523-548; Kazani, S and Israel, E (2010) "*Exhaled breath condensates in asthma: diagnostic and therapeutic implications*," J. Breath Res. 4:047001; Loukides, S et al. (2011), supra., Curr. Med. Chem. 18:1432-1443; Sack, U et al. (2006) "*Multiplex analysis of cytokines in exhaled breath condensate*," Cytometry A. 69:169-172; Bayley, D L et al. (2008) "*Validation of assays for inflammatory mediators in exhaled breath condensate*," Eur. Respir. J. 31:943-948; Sapey, E et al. (2008) "*The validation of assays used to measure biomarkers in exhaled breath condensate*," Eur. Respir. J. 32:1408-1409).

Another approach to collecting particles (e.g. such as RTLF droplets) from exhaled breath provides for the use of a conventional three-stage inertial impactor. Such impactors rely on inertia of the particles within a flow path. In particular, aerosol particles with greater inertia attach to a plate in the first stage, while those with less inertia flow through nozzles and enter into the following stages. Although such methods have been reported to successfully collect some protein from RTLF droplets, the obstacles with recovery from the impaction plate material have inhibited their use. Thus far, successful reports primarily require impaction onto silicon wafers and analysis by mass spectroscopy and are not amenable to other analytical techniques (e.g. immunoassay or PCR).

Accordingly, there is a need for systems and methods for collecting and analyzing exhaled breath aerosol that overcome some or all of the problems associated with conventional systems and methodologies.

SUMMARY OF THE INVENTION

The present invention is directed to gaseous fluid collection systems and methods for collecting and concentrating aerosol particles in the gaseous fluid. In a preferred embodiment, the system and method provides for the collection of exhaled breath aerosol (EBA) from exhaled breath of a subject. The EBA comprises RTLF droplets, which are concentrated in the collected sample. The EBA sample may then be analyzed to detect and study one or more target analytes. In accordance with preferred embodiments, the disclosed systems and methods provide for a laminar flow of exhaled breath (or other gaseous fluid sample) through a cooled flow channel or passage. The water vapor from the exhaled breath is condensed onto the walls of the cooled passage and removed from the gaseous fluid flow. In the absence of turbulence, little or none of the aerosol particles in the exhaled breath (or other gaseous fluid) is deposited on the interior walls of the passage, and thus is not mixed with the exhaled breath condensate. A substantial portion, and preferably substantially all, of the water vapor is extracted from the gaseous fluid flow. The remaining aerosol (e.g., RTLF droplets) is impacted onto a layer of ice.

The disclosed systems and methods exhibit numerous advantages over prior methodologies. The removal of most of the water vapor prior to impaction on ice substantially increases analyte concentration in the resulting sample. In addition, ice impaction provides a solid surface, thereby increasing the efficiency of impaction as compared with impingement in a liquid. Ice impaction also obviates the need to extract a collected sample from a solid surface, e.g., such as a filter, or metal or silicon impaction surface which results in loss and/or damage to the sample. Further, ice impaction immediately freezes the sample, thereby protecting molecules in the sample from degradation reactions that may occur in liquid samples or at higher temperatures.

The present invention relates to an aerosol collection system comprising an inlet portion configured to receive a gaseous fluid containing water vapor and aerosol particles. A primary passage in fluid communication with the inlet portion is configured to channel a flow of the gaseous fluid therethrough. An outlet portion in fluid communication with the primary passage is provided. A sample collection region is configured to receive from the outlet portion the aerosol particles, wherein the aerosol particles are impacted onto a layer of ice in the sample collection region. The system preferably includes at least one laminar flow chilled passage operably associated with the primary passage and configured to cool the gaseous fluid flow to a temperature sufficient to condense the water vapor passing therethrough. A first portion of the water vapor condenses onto the aerosol particles and thereby increases aerodynamic diameter of the aerosol particles. A second portion of the water vapor condenses on an interior surface of the laminar flow chilled passage. In some embodiments, the outlet portion comprises an acceleration nozzle configured to increase velocity of the aerosol particles for impaction onto the layer of ice.

In some embodiments, the system includes a flow dividing baffle operably associated with the laminar flow chilled passage and configured to duct the liquid water on the interior surface of the laminar flow chilled passage away from the primary passage.

In some embodiments, the system includes a size selection impactor, which may be either a conventional inertial impactor or a virtual impactor. The size selection impactor is in fluid communication with the primary passage and upstream from the laminar flow chilled passage. The size selection impactor is configured to separate and remove aerosol particles having a diameter greater than a preselected size away from the primary passage.

In some embodiments, the system comprises at least one concentrator virtual impactor in fluid communication with the primary passage and downstream from the laminar flow chilled passage. The concentrator virtual impactor is configured to divide the gaseous fluid flow into a major flow and a minor flow. Aerosol particles are concentrated in the minor flow and a portion of the water vapor is directed into the major flow. In some implementations, the system includes a plurality of concentrator virtual impactors, which may be provided in series, and in fluid communication with the primary passage. In some implementations, the aerosol particles are concentrated at least about 10-fold in the minor flow and at least about 90% of the water vapor is directed into the major flow.

In some implementations, the system includes a secondary passage in fluid communication with the size selection impactor. Aerosol particles having a diameter greater than a preselected size flow into the secondary passage. In some implementations, the system comprises at least a second laminar flow chilled passage operably associated with the secondary passage and configured to cool the gaseous fluid flow in the secondary passage to a temperature sufficient to condense the water vapor. A portion of the water vapor condenses onto the aerosol particles and thereby increases an aerodynamic diameter of the aerosol particles. Another portion of the water vapor condenses on an interior surface of the second laminar flow chilled passage. In some implementations, the system further comprises a second flow dividing baffle operably associated with the second laminar flow chilled passage and configured to duct liquid water on the interior surface of the second laminar flow chilled passage away from the secondary passage.

In some embodiments, the system comprises at least one concentrator virtual impactor in fluid communication with the secondary passage and downstream from the second laminar flow chilled passage. The concentrator virtual impactor is configured to divide the gaseous fluid flow into a major flow and a minor flow. Aerosol particles are concentrated in the minor flow and a portion of the water vapor is directed into the major flow. In some embodiments, the secondary passage is in fluid communication with a second outlet portion. The second outlet portion is downstream from the second laminar flow chilled passage. The system further comprises a second sample collection region configured to receive from the second outlet portion the aerosol particles, wherein the aerosol particles are impacted onto a layer of ice in the second sample collection region.

In some embodiments, the system comprises a heating device upstream from the laminar flow chilled passage. The heating device is configured to maintain the gaseous fluid flow in the primary passage at a preselected temperature. In some embodiments, the system comprises a droplet counting system operably associated with the primary passage and configured to determine number and size distribution of the aerosol particles.

The present invention also relates to a method of collecting and analyzing aerosol particles from a gaseous fluid. The disclosed method comprises the steps of: collecting a gaseous fluid containing water vapor and aerosol particles; directing a flow of the gaseous fluid through a laminar passage; cooling the gaseous fluid flow in the laminar passage to a temperature sufficient to condense the water vapor, wherein a portion of the water vapor condenses onto the aerosol particles and thereby increases an aerodynamic diameter of the aerosol particles, and another portion of the water vapor condenses on an interior surface of the laminar passage. At least a portion of the condensed water vapor on the interior surface is removed from the gaseous fluid flow in the laminar passage. Aerosol particles in the gaseous fluid flow are then impacted onto a layer of ice after the removing step, thereby forming a frozen sample comprising the aerosol particles.

In some embodiments, the disclosed method comprises the further steps of: melting the frozen sample; and detecting one or more biomarkers in the melted sample. The biomarkers may be associated with any target analyte, e.g., including but not limited to a biomarker associated with a biological agent, explosive, or disease, disorder or infection.

BRIEF DESCRIPTION OF THE DRAWINGS

FIG. 6 illustrates a collection cup of a sample collection region in accordance with a disclosed embodiment.

FIG. 6A is a cross sectional view of the collection cup according to a disclosed embodiment.

DETAILED DESCRIPTION OF EMBODIMENTS OF THE INVENTION

Figure 1:
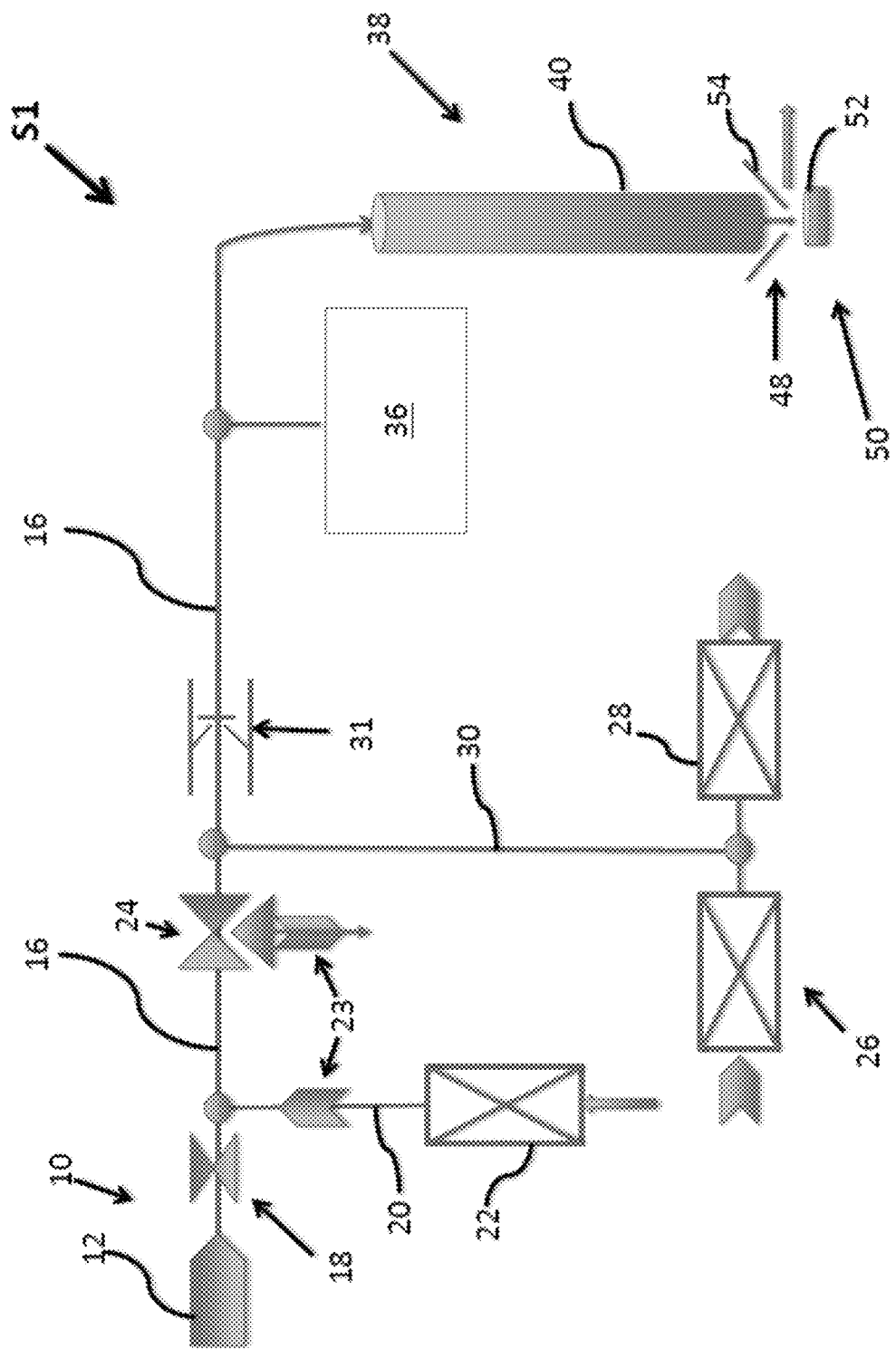
FIG. 1 illustrates schematically an exhaled breath aerosol collection system according to an embodiment of the present invention.

The present invention relates to systems and methods for collecting and analyzing bioaerosols in a gaseous fluid. In preferred embodiments, the disclosed systems and methods are configured for collecting and analyzing exhaled breath aerosol (EBA) from exhaled breath from a subject, e.g., such as a mammal, preferably a human. In a preferred embodiment, an aerosol collection system includes an inlet portion configured to receive a gaseous fluid containing water vapor and aerosol particles. A primary passage is in fluid communication with the inlet portion and configured to channel a flow of the gaseous fluid therethrough. The system includes one or more laminar flow chilled passage(s) operably associated with the primary passage and configured to cool the gaseous fluid flow to a temperature sufficient to condense the water vapor in the gaseous fluid flow, and additionally grow the aerosol particles to a larger aerodynamic diameter. A small amount of the water vapor condenses onto the aerosol particles and thereby increases aerodynamic diameter of the aerosol particles. However, the vast majority (and preferably substantially all) of the water vapor condenses into liquid water on an interior surface of the laminar flow chilled passage (e.g., the interior surface(s) or wall(s) of the region(s) or portion(s) of the primary passage (in fluid communication with the primary passage) which define the laminar flow chilled passage(s)). The liquid water on the interior surface is ducted away and removed from the primary passage, preferably via a flow dividing baffle system operably associated with the laminar flow chilled passage. An outlet portion downstream from the laminar flow chilled passage is in fluid communication with the primary passage. A sample collection region is provided, which is configured to receive from the outlet portion the aerosol particles, wherein the aerosol particles are impacted onto a layer of ice in the sample collection region.

In preferred embodiments, the disclosed systems and methods involve cryogenic impaction for collection of exhaled breath aerosol particles. The disclosed systems demonstrate a substantially greater recovery of non-volatile protein biomarkers from EBA as compared to previously reported systems. In some implementations, the disclosed systems demonstrate recovery of non-volatile protein biomarkers from EBA more than 4 times greater as compared to recovery demonstrated by prior systems. In some implementations, the disclosed systems demonstrate more than about 10 times, or more than about 100 times, or more than about 200 times, or more than about 300 times, or more than 350 times, greater recovery of non-volatile protein biomarkers from EBA as compared to the recovery demonstrated by prior systems.

In addition, the disclosed systems demonstrate a substantially greater concentration of protein biomarkers in the final sample as compared to previously reported systems. In some implementations, the disclosed systems demonstrate at least about 4-fold greater, or at least about 8-fold greater, or at least about 10-fold greater, or at least about 20-fold greater, or at least about 30-fold greater, or at least about 36-fold greater concentration of protein biomarkers in the final sample as compared to results reported by prior methodologies.

In accordance with disclosed embodiments, the collection system concentrates the aerosol and then impacts the concentrated aerosol on an extremely thin layer of ice. Prior to impaction, excess water from condensation of saturated water vapor in the exhaled breath (or other gaseous fluid) is ducted away from the laminar flow of gaseous fluid via a flow divider system, thereby avoiding dilution of the resulting sample with the condensed water vapor. As known in the art, exhaled breath exits a subject at body temperature (~37° C.) and pressure (generally same as ambient), saturated (~6.2 kPa). As the exhaled breath air stream cools in the flow channel or primary passage of the collection system, water vapor condenses on the cool interior surfaces of the passage into liquid water. A small fraction of the water vapor also condenses on the aerosol particles (e.g., a few femto-liters of water vapor), as discussed in further detail below. The collection systems of the present invention remove a large portion, and preferably substantially all, of the condensed water vapor on the interior surface of the passage, so that the resulting sample is primarily only aerosol particles (e.g., EBA particles).

As noted above, samples collected using conventional EBC sampling systems contain a significant amount of water (>99%) and thus result in extremely low analyte concentrations, particularly non-volatile biomarkers (e.g. see U.S. Pat. Nos. 7,118,537; 7,547,28; and 8,491,494; WO 2015/015201 A1; U.S. Patent Application Publication No. 2008/0214947; see also Muccilli, V. et al. (2015) "*Protein profile of exhaled breath condensate determined by high resolution mass spectrometry*," J. Phann. Biomed. Anal., 105:134-149; and Horvath, I. et al. (2005) "*Exhaled breath condensate: methodological recommendations and unresolved questions*," Eur. Respir. J. 26(3):523-48).

The disclosed systems provide for condensation of water vapor from the exhaled breath (or other gaseous fluid) as the exhaled breath is directed through laminar flow tubes or passages. In addition, a small portion of the water vapor condenses onto aerosol particles present in the exhaled breath (or gaseous fluid), thereby increasing the size and average aerodynamic diameter of the particles. The aerosol particles are grown in the laminar flow chilled passage(s) from fine and ultrafine aerosol droplets to a size that allows for optimal and efficient impaction using an acceleration nozzle to surface impactor (e.g., wherein the grown aerosol droplets preferably have a final size of at least about 1 μm, more preferably between about 1 μm to about 2.5 μm aerodynamic diameter). The disclosed systems exhibit an efficiency of virtually 100% for aerosol droplets having a size of >0.006 μm in diameter (e.g., utilizing laminar flow chilled passage(s) maintaining the gaseous fluid flow at a temperature of 0° C. or less), which is an order of magnitude smaller as compared to prior reported collection systems.

The aerosol particles are impacted onto an extremely thin layer of ice having a relatively small total volume, e.g., between about 2.5 μL to about 1500 μL, more preferably between about 2.5 μL to about 500 μL, or between about 2.5 μL to about 100 μL, or between about 2.5 μL to about 25 μL. By melting the ice, the resulting concentrated aerosol sample allows for essentially 100% recovery into solution or suspension in aqueous media of infectious agents and biomarkers from the aerosol. In the disclosed systems, there are virtually no losses due to extraction, as compared to extraction from a solid dry impaction substrate (e.g., see U.S. Patent Application Publication No. 2010/0297635). Upon impaction into the layer of ice, the aerosol particles are immediately frozen and thus the molecules in the sample are protected from degradation reactions that may otherwise occur in liquid samples or at higher temperatures. As such, the disclosed systems provide for virtually no loss of activity due to enzymatic or other degradation or inactivation reactions, e.g., such as in conventional systems providing for collection in a liquid aqueous media such as many breath condensate systems.

Thus, after impaction of the aerosol particles into ice, the frozen sample may be readily melted for further analysis. The melting of the ice sample produces a liquid sample immediately available for analysis either in an online on-chip assay or in an off-line laboratory assay. The sample may include various particles including but not limited to proteins, bacteria, viruses, nucleic acids (DNA, RNA), lipids, peptides, nucleotides, sugars, and/or other volatile, nonvolatile and/or semi-volatile organic molecules arising from the RTLF. Analysis of a wide range of molecules that are biomarkers for exposures associated with biowarfare agents (e.g., biological toxins, infectious agents such as bacteria, viruses, fungi, and/or other biological or chemical warfare agents), toxic or immunogenic agents, pollutants, explosives, metabolic processes, diseases, disorders, infections, drug delivery to the lungs, and/or other conditions is possible utilizing the disclosed systems and methods. For example, a sample may be analyzed for biomarkers associated with a hazardous exposure, respiratory disease, disorder or infection, e.g., including but not limited to lung cancer, asthma, chronic obstructive pulmonary disease, tuberculosis, influenza, a human immunodeficiency virus (HIV) related infection, an acquired immune deficiency syndrome (AIDS) related infection, a respiratory syncytial virus (RSV) related infection, an adenovirus related infection, a coronavirus related infection (e.g., severe acute respiratory syndrome coronavirus (SARS-CoV), Middle East respiratory syndrome coronavirus (MERS-CoV)), a Legionnella related infection or disease, a *Bordetella pertussis* related infection, and/or a measles virus related infection. In some implementations, the biomarker(s) is microRNA (miRNA) and/or exosome complex. In other implementations, the biomarker(s) comprise cytokines including but not limited to IFN-gamma, IL-1 beta, IL-7, IL-8, IL-13, and TNF-alpha).

In some implementations, the impaction ice layer is seeded with an appropriate buffer or stabilizer that mixes with the collected sample upon melting, thus further protecting the sample from degradation or inactivation. In one implementation, the impaction ice layer is seeded with an appropriate reagent that stabilizes RNA and/or inhibits proteolysis (e.g., Ribonuclease (RNase) and/or protease inhibitors). Alternative or additional buffers suitable for stabilizing the sample would be readily apparent to those of ordinary skill, e.g. including but not limited to phosphate buffered saline (PBS), 3-{[tris(hydroxymethyl)methyl]-amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 4-2-hydroxyethyl-1-piperazine-ethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate) and 2-(N-morpholino)ethanesulfonic acid (MES).

Figure 2:
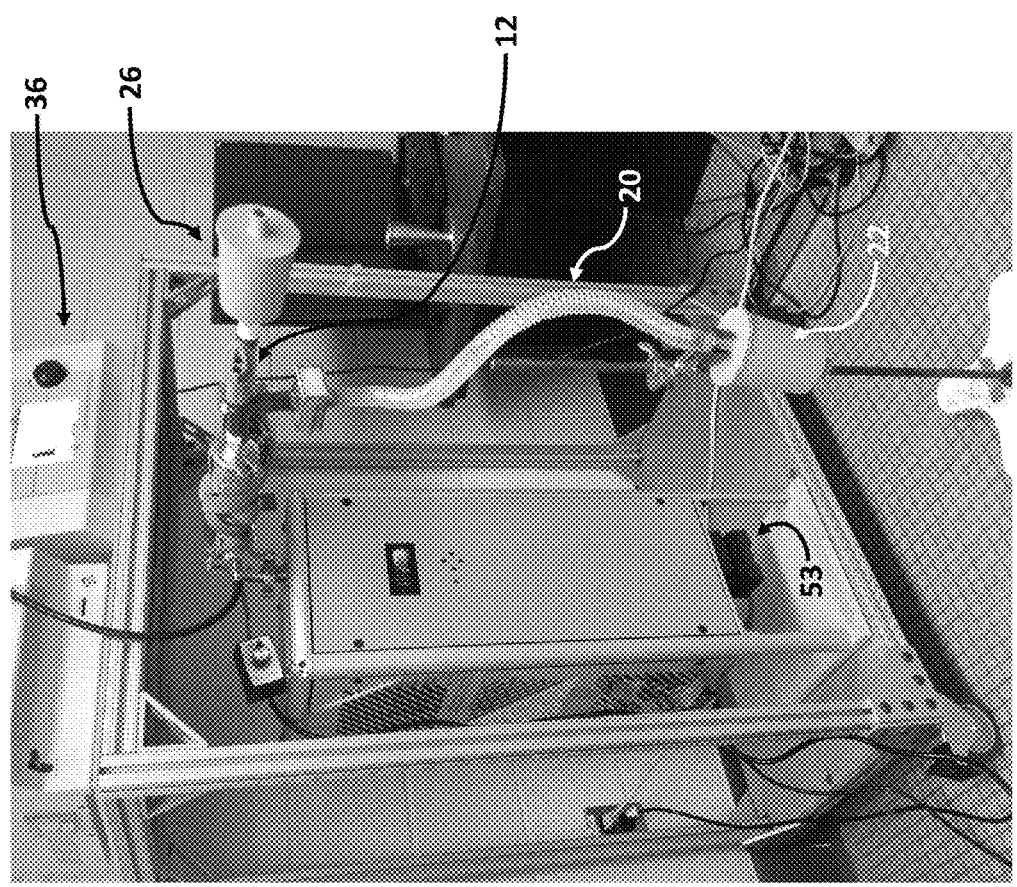
FIG. 2 is an image of an exhaled breath aerosol collection system according to an embodiment of the present invention.

Referring to FIGS. 1 and 2, an exemplary aerosol collection system S1 in accordance with an embodiment of the present invention is illustrated. As apparent to those of skill in the art, the specific configurations and lengths of the flow channels or passages of the disclosed EBA collection systems, as well as selected flow rates and temperatures, and sufficient cooling to prevent melting of and maintain the desired temperature of the ice impaction surface, may be optimized to achieve the desired growth characteristics of the aerosol particles. For example, mathematical modeling software (e.g., COMSOL MULTIPHYSICS®) may be utilized for developing specific passage configurations and optimizations.

Figure 3:
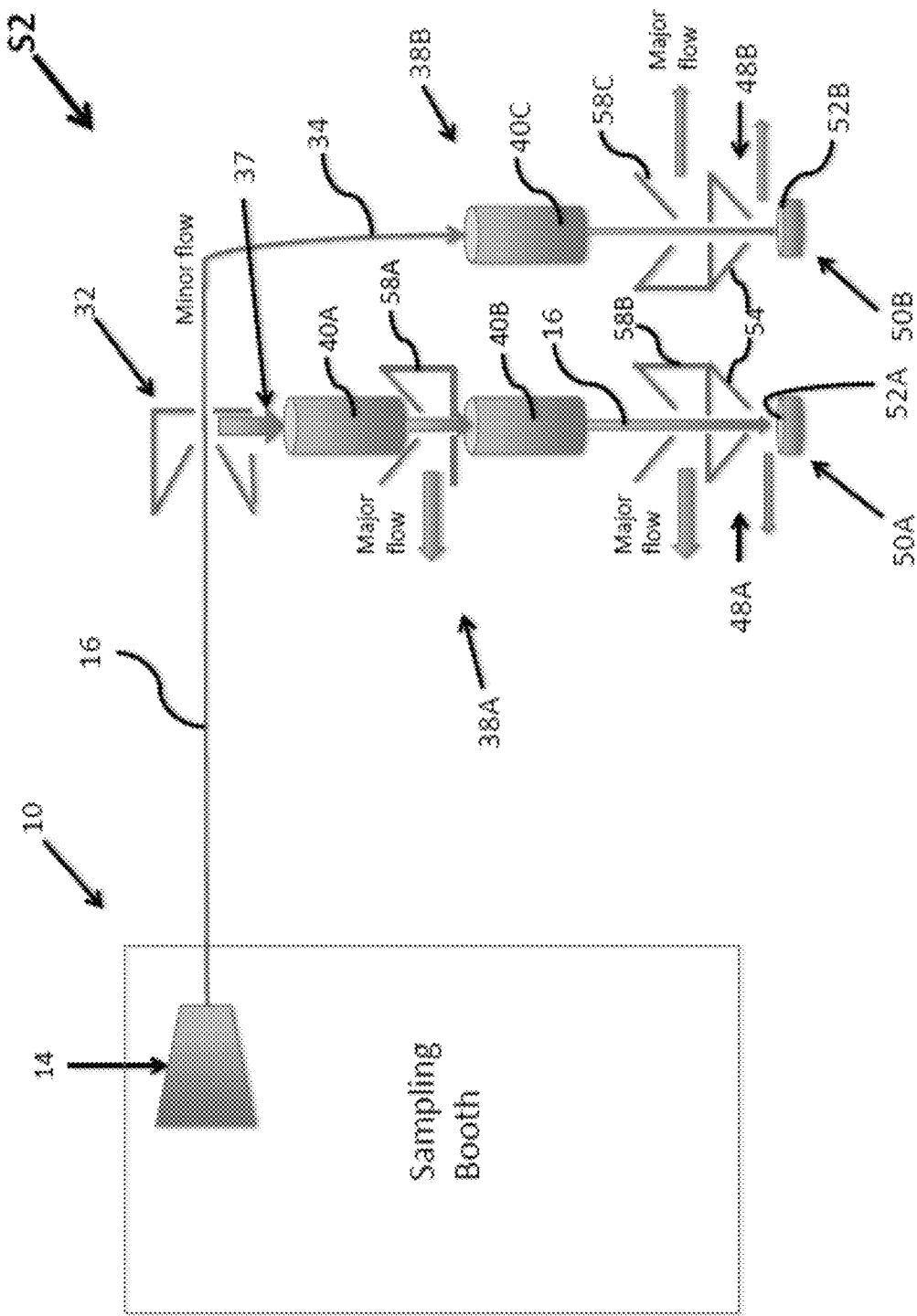
FIG. 3 illustrates schematically an exhaled breath aerosol collection system according to another embodiment of the present invention.

The system S1 includes an inlet portion 10 configured to receive or input a gaseous fluid containing aerosol particles and water vapor, e.g., such as exhaled breath from a human subject. In some implementations, the inlet portion 10 includes a mouthpiece 12 into which the subject breathes. In some implementations, humidified, filtered air may be injected into the inlet portion 10 via a supply channel 20. Alternatively, or in addition, an aerosol collection system S2 may include an inlet portion 12 having a cone-shaped mouthpiece, or personal cloud aerosol capture cone 14, into which the subject breathes, such as shown in FIG. 3. A seating area may also be provided for the subject, which may be tented or enclosed. In some implementations, such as in relatively dry environments, a humidifier is provided within the tented area in order to increase moisture content therein.

Referring again to FIG. 1, the inlet portion 10 is in fluid communication with a flow channel or primary passage 16 through which the exhaled breath or gaseous fluid flows. In some implementations, a flow sensor device 18 (e.g., an ultrasonic flow meter) is provided downstream from and proximate to the mouthpiece 12 for measuring and monitoring air flow velocity and volume as the gaseous fluid flow enters the primary passage 16. An air supply channel 20, preferably containing a high efficiency particulate air (HEPA) filter 22, may be provided downstream from the mouthpiece 12, which is in fluid communication with the primary passage 16 and supplies warm, humid, HEPA filtered air for inhalation by the subject. If the environment in the primary passage 16 is not sufficiently humid, aerosol particle growth may be hampered. In some implementations, the gaseous fluid flow is channeled through a 1-way valve(s) 23 provided in the primary passage. In other implementations, the gaseous fluid flow proceeds through a 3-way valve 24 in fluid communication with the primary passage 16, as shown in FIG. 1. Extraneous material in the exhaled breath is channeled out of the primary passage 16 through a 1-way valve 23 coupled to or integrated with the 3-way valve 24 during a wash-out period at the start of breath sampling. In other implementations, the 1-way valve 23 is provided on the air supply channel and/or a pressure equalization system 26. The 1-way valve 23 helps to stabilize the flow of gaseous fluid and maintain a unidirectional flow through the passage (e.g., such as during inhalation by the subject utilizing the system), and also may be beneficial in some configurations including particle counting instrumentation that is highly sensitive to pressure drop in the system S1.

Figure 5:
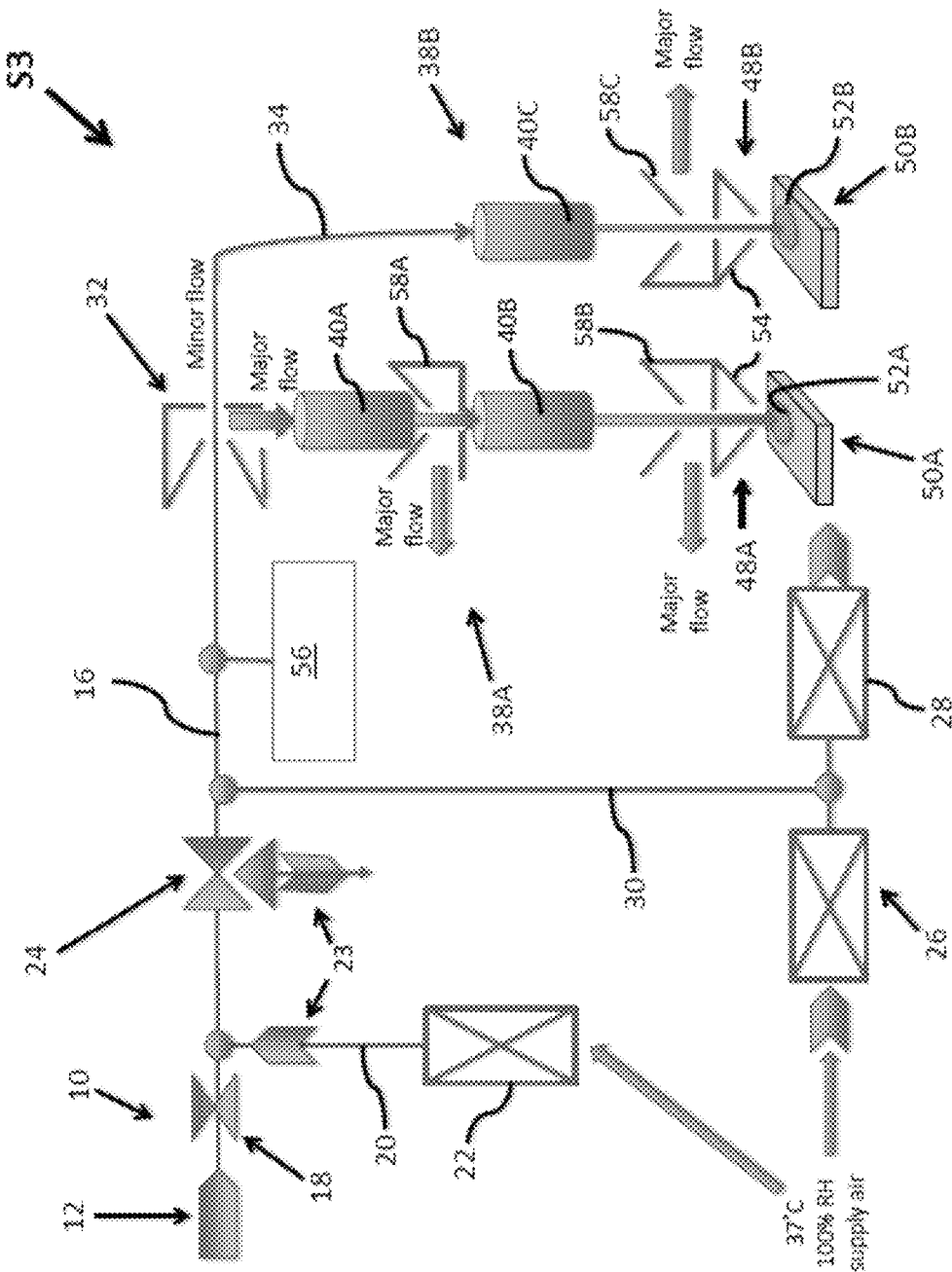
FIG. 5 illustrates schematically an exhaled breath aerosol collection system according to another embodiment of the present invention.

With continued referenced to FIG. 1, the pressure equalization device 26 preferably includes a filter system 28 (e.g., including one or more HEPA filters) and supply channel 30 in fluid communication with the primary passage 16 and downstream from the 3-way valve 24. Thus, a pressure equalized air stream may be supplied to the primary passage 16 via the pressure equalization device 26. In some embodiments, the gaseous fluid flow is then directed to a size selection inertial impactor 31 (FIG. 1) or virtual impactor 32 (FIGS. 3 and 5). It is believed that different size aerosol particles in exhaled breath are generated at different levels in the lungs and/or by different processes. Thus, the differently sized aerosol particles contain biomarkers originating from or associated with different locations within the airways and/or from different metabolic processes. Thus, segregation of the particles into two or more size categories (or removal of larger particles as in FIG. 1) is advantageous for some applications and analysis.

As known in the art, a virtual impactor (VI) is a device configured to segregate particles based on aerodynamic size, and thus concentrate particles. Unlike a conventional inertial impactor, a VI does not have solid collection surfaces. Rather, particles are inertially sampled from a large flow to a smaller sub-flow. The initial or primary sampled flow is channeled through an inlet of the VI, and the flow is then split into major and minor flows (e.g., about 90% may be directed into a major flow, and about 10% may be directed into a minor flow). Particles having a large enough inertia (e.g., having an aerodynamic diameter greater than a predetermined size) follow the minor flow, while particles with a smaller inertia (e.g., having an aerodynamic diameter less than the predetermined size) are channeled along the major flow stream and continue through the primary passage 16, as shown in FIG. 3. Thus, the total volume of gaseous fluid is reduced in the minor flow (compared to the flow of gaseous fluid prior to entering the VI), thereby concentrating the larger aerosol particles in a smaller amount of gas.

Thus, as the gaseous fluid flow enters the size selection impactor 31 or 32 from the primary passage 16, larger aerosol particles having an aerodynamic diameter greater than a predetermined size (e.g. about 10%) follow a minor flow into a secondary passage 34, and smaller aerosol particles having an aerodynamic diameter less than the predetermined size (e.g., about 90%) follow a major flow into the primary passage 16 (see FIG. 3). In one implementation, the size selection VI 32 is configured to direct aerosol particles having a diameter greater than about 2.5 µm into the secondary passage 34 and away from the primary passage 16. However, it should be understood that the size selection VI 32 may be configured to separate and remove particles having a diameter less than (or greater than) 2.5 µm, and thus the size selection is not limited to the exemplary embodiment described herein. Furthermore, if the larger aerosol particles are not of interest, a conventional inertial impactor 31 (see FIG. 1) could be provided in the primary passage 16, which is configured to remove the larger aerosol particles from the gaseous fluid flow via an impaction surface. Such conventional impactor 31 would decrease loss of the smaller aerosol particles (given 10% of the smaller aerosol particles pass along in the minor flow of a VI).

In some embodiments, a droplet counting and sizing device 36 is provided downstream from the size selection impactor 31 or 32 and/or inlet portion 10 (e.g., if a size selection impactor 31 or 32 is not provided in the system configuration), and operably associated with the primary passage 16 (see FIG. 1) and/or secondary passage 34 (see FIG. 3). For example, an optical particle counter may be provided, which determines the number and size distribution of aerosol particles within the primary passage 16. In some embodiments, a steam injector 37 may be provided (FIG. 3) which injects steam into the major flow of gaseous fluid via a supply channel downstream from the size selection impactor 31 or 32.

The gaseous fluid flow within the primary passage 16 is then directed into a water vapor extraction region 38 in fluid communication with the primary passage 16. The water vapor extraction region 38 is configured to remove condensed liquid water away from and out of the gaseous fluid flow in the primary passage 16 and/or secondary passage 34. In a preferred embodiment, the water vapor extraction region 38 comprises at least one laminar flow chilled passage 40 operably associated with or defining a portion or region of the primary passage 16, and configured to cool the gaseous fluid flow F (see FIG. 4) therein to a temperature sufficient to condense water vapor in the gaseous fluid (e.g., exhaled breath). In addition, the temperature is also sufficiently low such that the ice impaction surface 52 (discussed in further detail below) is not melted. In one implementation, the laminar flow chilled passage 40 is configured to cool the air stream to a temperature just above 0° C. A chiller device or cooling mechanism is operably associated with the laminar flow chilled passage 40, which is configured to cool a laminar flow region or portion of the primary passage 16, which region or portion defines the laminar flow chilled passage. Such chiller devices or cooling mechanisms are well known in the art. Thus, any means or device capable of chilling the fluidic flow within the passage may be utilized.

Figure 4:
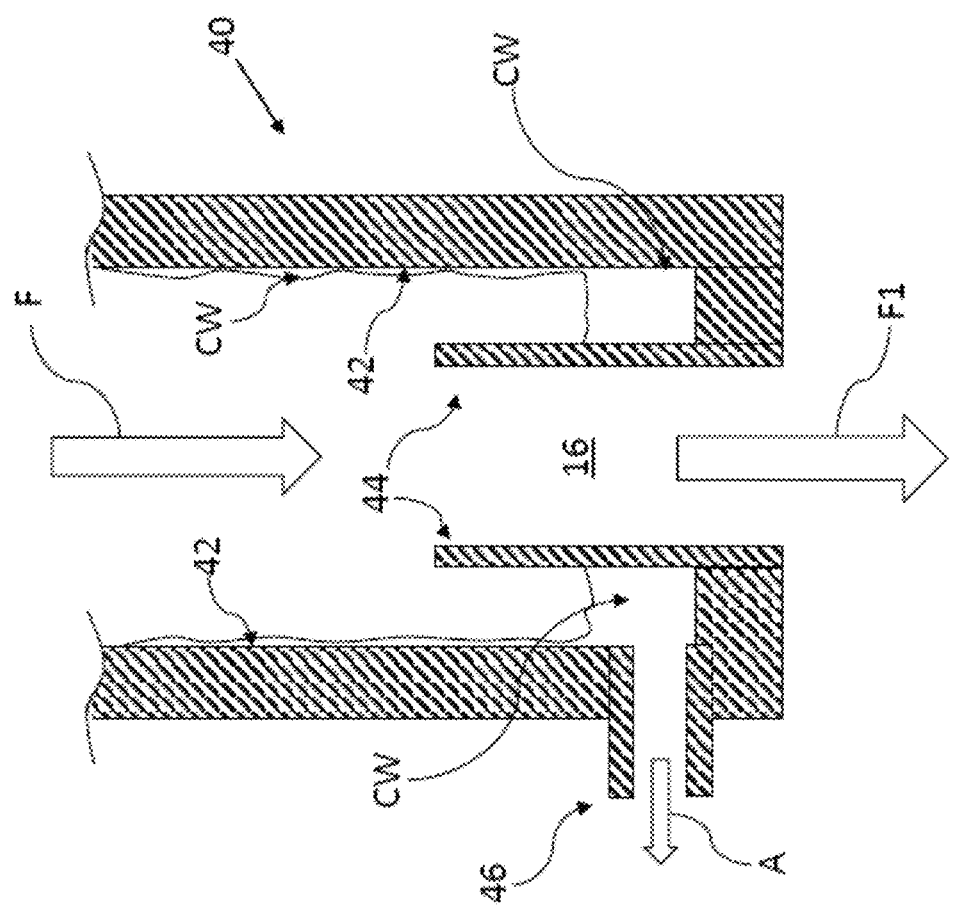
FIG. 4 is a cross sectional view of portions of a laminar flow chilled passage and drain of an aerosol collection system in accordance with disclosed embodiments and showing removal of condensed liquid water from the gaseous fluid flow.

In the laminar flow chilled passage 40, a vast majority of the water vapor (e.g., up to ~90%) in the exhaled breath condenses primarily on the cold interior surfaces 42 of the primary passage 16 within the water vapor extraction region 38 (FIG. 4). The condensate CW may be in the form of liquid water (see FIG. 4) or as ice. However, a small amount of water vapor also condenses onto the aerosol particles in the laminar fluid flow F, thereby causing the aerosol particles to increase in aerodynamic diameter and 'grow' into larger aerosol particles. The water vapor extraction region 38 additionally comprises a flow dividing structure configured to separate and remove condensed liquid water CW on the interior surfaces 42 of the primary passage 16. In one implementation, the flow dividing structure comprises a flow divider baffle system 44. Condensed water CW on the surfaces 42 of the primary passage 16 is ducted away from the primary passage 16 via a drain or water outlet 46 operably associated with the flow divider baffle 44 (shown by arrow A). The gaseous fluid flow F passes through the laminar flow chilled passage 40, cooling the gaseous flow F and removing condensed water vapor CW. The gaseous fluid flow then exits the laminar flow chilled passage 40 (shown by arrow F1) and continues along in the primary passage 16; the resulting gaseous flow F1 includes larger aerosol particles (grown via small amounts of water vapor thereon to increase inertia for impaction) carried in gaseous fluid with a lower water vapor content than the starting aerosol.

Coupled to and in fluid communication with the primary passage 16 in the water vapor extraction region 38 is an outlet portion 48, as shown in FIG. 1. The remaining gaseous fluid flow (which includes a high concentration of aerosol particles at this stage) is channeled along the primary passage 16 from the laminar flow chilled passage 40 through the outlet portion 48 and toward a sample collection region 50. The sample collection region 50 comprises an impaction surface 52 configured to receive the aerosol particles from the outlet portion 48. In a preferred embodiment, a nozzle to surface impactor is provided. The outlet portion 48 includes an acceleration nozzle 54 configured to increase mean velocity of the grown aerosol particles for impaction against the impaction surface 52. In addition, remaining water vapor condensed near the impaction surface is directed away from the impaction surface, thereby reducing the potential dilution of the EBA particles in the resulting sample by condensation around the target ice impaction surface. Preferably, at least about 75%, more preferably at least about 85%, of the condensed water vapor from the gaseous fluid (e.g., exhaled breath) is removed by the disclosed systems and methods. In particularly preferred embodiments, a substantial portion (at least about 85%), and more preferably substantially all (at least about 95% or more) of the water vapor from the exhaled breath is removed by the disclosed systems and methods through a combination of condensation and aerosol concentration. For example, from a psychometric chart at 37° C., the moisture in the air is about 43.9 g/m$^3$ and at 0° C. it is about 4.8 g/m$^3$. In one implementation, the disclosed system removes about 89% of water vapor by condensation. In other implementations including one or more aerosol concentrating VIs, additional removal of condensed water vapor is achieved. For example, if a single 90:10 VI is provided in the system, then 43.9 g/m$^3$×1 m$^3$->4.8 g/m$^3$×0.1 m$^3$ results in ~99% reduction in water vapor. If such a system includes a second VI, a 99.9% reduction in water vapor is achieved.

The impaction surface 52 comprises an extremely thin layer of ice, which is maintained at an extremely low temperature via an associated cooler device 53 (see FIG. 2) and immediately freezes the aerosol particles upon impaction, thereby protecting the aerosol particles from degradation. In preferred embodiments, the layer of ice is maintained at a temperature of less than about −1° C., preferably between about −1° C. and about −20° C., more preferably between about −10° C. and about −16° C. Cryogenic impaction provides numerous advantages as compared to prior art systems. The ice layer provides a solid surface for impaction, yet obviates the need for extraction of the collected sample (given the frozen sample may be simply melted for analysis as noted above).

In addition, the layer of ice has a relatively small volume, e.g., preferably between about 2.5 μL to about 1500 μL, or between about 2.5 μL to about 500 μL, and more preferably between about 2.5 μL to about 100 μL, or between about 2.5 μL to about 25 μL. Thus, the collected EBA sample comprises a relatively small amount of water when melted for analysis given a vast portion, and preferably a substantial portion, or substantially all, of the water vapor in the exhaled breath condensate is eliminated from the sample. Thus, the amount of water vapor that is left to condense on the ice impaction surface is minimized or essentially eliminated, with only aerosol particles (e.g., RTLF droplets with a few femtoliters of additional water condensation per droplet) impacted onto the ice layer. In this way, the volume of water in the resulting sample is minimized, thereby substantially increasing the concentrations of target analytes in the resulting sample. Accordingly, the disclosed systems are suitable for marrying to microfluidic lab on a chip technologies.

Referring to FIG. 5, an advanced EBA collection system S3 in accordance with another embodiment is illustrated. The advanced EBA collection system S3 provides for aerosol particle growth and water vapor extraction as described above. Accordingly, features and components described above are identified with like reference numbers. Accordingly, the advanced EBA collection system S3 includes an inlet portion 10 configured to receive exhaled breath from a subject, which may include a mouthpiece 12 into which the subject breaths. In addition, the mouthpiece 12 may be operably coupled to a heating device for maintaining the interior space of the mouthpiece 12 and associated tubing at a predetermined temperature (e.g. 37° C.). Additionally, in preferred embodiments the advanced EBA collection system S3 comprises a flow sensor 18 (e.g., an ultrasonic flow meter), a supply channel 20 through which filtered air is supplied, and a 3-way valve 24 for washout. The components are all in fluid communication with a primary passage 16 as described above.

The advanced system S3 may include a HEPA filtered pressure equalization device 26 downstream from the 3-way valve 24, as described above. Additionally, the advanced system S3 may include a humidifier/heater coupled to and in fluid communication with the HEPA filter, pressure equalization device and/or primary passage upstream from a size selection VI 32. The humidifier/heater is configured to increase moisture content (e.g., 100% relative humidity) of the gaseous fluid flow within the primary passage 16 upstream from the size selection impactor 32 (or 31), and additionally maintain the temperature within the primary passage 16 upstream from the size selection VI 32 at a predetermined temperature (e.g. 37° C.). However, a laminar fluid flow is maintained within primary passage 16 (as opposed to a turbulent flow such as provided in conventional EBC collectors).

Additionally, in some embodiments the advanced system S3 comprises particle counting and sizing device 56 (e.g., an isokinetic probe and parallel droplet counting and sizing device), which is upstream from a size selection VI 32. The size selection VI 32 segregates particles based on size, inertially sampling the aerosol particles from the incoming larger flow of gaseous fluid from the primary passage 16. As described above, the larger fluid flow is channeled through an inlet of the size selection VI 32, and the fluid flow is then split into major and minor flows (e.g., 90% and 10%, respectively) via the size selection VI 32. Particles having a large enough inertia (e.g., having a diameter greater than a predetermined size, e.g. 2.5 μm) follow a minor flow stream into a secondary passage 34 (see FIGS. 3 and 5), while aerosol particles with a smaller inertia (e.g., having a diameter less than the predetermined size, e.g. 2.5 μm) follow a major flow and continue along through the primary passage. Note that aerosol particles segregated by the size selection VI 32 have preferably not yet been grown in the described embodiment and have been maintained at close to their original size by maintaining a predetermined temperature and relative humidity in the primary passage. The size selection VI thus separates out the smallest and largest particles, thus allowing for two or more size fractions to be collected.

With continued reference to FIG. 5, the major flow (comprising smaller aerosol particles) continues along within the primary passage 16 and is then directed into a first water vapor extraction region 38A in fluid communication with the primary passage 16. The first water vapor extraction region 38A is configured to duct condensed liquid water away from and out of the primary passage 16, and comprises a first laminar flow chilled passage 40A, which includes a flow divider baffle system 44 as described above (see FIG. 4). In addition, aerosol particles are grown into larger aerosol particles within the first laminar flow chilled passage 40A of the first water vapor extraction region 38A. The cooled fluid flow from the first laminar flow chilled passage 40A is then directed through a first concentrator VI 58A (see FIGS. 3 and 5). The first concentrator VI 58A is configured to direct a major portion of the gaseous fluid flow (e.g. about 90%) containing most of the water vapor (e.g. about 90%) out of the primary passage 16 in the major flow. The first concentrator VI 58A directs a minor portion of the gaseous fluid flow (e.g. about 10%), which includes virtually all of the grown EBA particles and a minor portion of the remaining water vapor, along the primary passage 16 in the minor flow.

In some embodiments, the first water vapor extraction region may include a second laminar flow chilled passage 40B and/or associated second concentrator VI 58B, which function as described above. Thus, the minor flow in the primary passage 16 may be directed from the first concentrator VI 58A into a second laminar flow chilled passage 40B and/or second concentrator VI 58A. The gaseous fluid flow is again chilled in the second laminar flow chilled passage 40B, for example to a temperature near about 0° C. Additional water vapor condenses on the interior surface of the primary passage 16 within the second laminar flow chilled passage 40B, and is removed via a flow divider baffle system 44 and associated outlet 46. The further cooled fluid flow then proceeds from the second laminar flow chilled passage 40B into the second concentrator VI 58B, which directs a major portion of the entering gaseous fluid flow (e.g. about 90%) into a major flow, and a minor portion entering gaseous fluid flow (e.g., about 10%) into a minor flow along the primary passage 16.

The remaining minor flow in the primary passage 16 (comprising primarily only the smaller EBA particles, now grown and having significant inertia, and virtually no water vapor) is directed from the second concentrator VI 58B through an outlet portion 48A and into a first sample collection region 50A, preferably via an acceleration nozzle 54. The first sample collection region 50A includes an impaction surface 52A comprising a layer of ice, as described above. The EBA particles are thereby cryogenically impacted into the ice layer.

With continued reference to FIGS. 3 and 5, the minor flow of the gaseous fluid flow (comprising the larger aerosol particles) separated by the size selection VI 32 is directed into the secondary passage 34. The minor flow in the secondary passage 34 is directed into a second water vapor extraction region 38B in fluid communication with the second passage 34. The second water vapor extraction region 38B is configured to duct condensed liquid water away from and out of the secondary passage 34, and comprises a laminar flow chilled passage 40C, which includes a flow divider baffle system 44 as described above (see FIG. 4). In addition, the aerosol particles are grown into even larger aerosol particles within the laminar flow chilled passage 40C. The cooled fluid flow from the laminar flow chilled passage 40C is then directed through a concentrator VI 58C (see FIGS. 3 and 5). The concentrator VI 58C is configured to direct a major portion of the gaseous fluid flow (e.g. about 90%) containing most of the water vapor (e.g. about 90%) out of the secondary passage 34 in a major flow. The concentrator VI 58C directs a minor portion of the gaseous fluid flow (e.g. about 10%), which includes virtually all of the grown EBA particles and a minor portion of the remaining water vapor, along the secondary passage 34 in the minor flow.

The remaining minor flow in the secondary passage 34 (comprising primarily only the larger EBA particles, grown and having significant inertia, and virtually no water vapor) is directed from the concentrator VI 58C through an outlet portion 48B and into a second sample collection region 50B, e.g., via an acceleration nozzle 54. The second sample collection region 50B includes an impaction surface 52B comprising a layer of ice, such that the collected aerosol particles are cryogenically impacted into the ice layer.

The specific configuration of the sample collection region(s) 50 may vary depending on the particular configuration of the primary and/or secondary passages 16, 34 and associated laminar flow passage(s) 40 and/or impactor(s) 58 utilized. The specific configuration of the sample collection region(s) 50 may also vary depending on the particular application and/or desired target analyte(s) being collected. In one embodiment, the sample collection region(s) 50 comprises a collection cup 60 configured to receive and maintain the thin layer of ice for impaction, as shown in FIGS. 6 and 6A. The collection cup 60 includes an inner cup portion 62 and an outer trough portion 64. In one implementation, the inner cup portion 62 includes sidewalls 66 and a base portion 68 defining an inverted conical recess 70 in which the ice layer is disposed, as best shown in FIG. 6A. The outer trough portion 64 includes an outer sidewall 72, a floor 74, and an inner sidewall 76 connected to and/or defining a portion of the sidewalls 66 of the inner cup portion 62.

As known in the art, when the air stream (e.g., flow F1) containing the enlarged particles leaves the nozzle (e.g., acceleration nozzle 54) and moves toward the impaction surface (e.g., the thin layer of ice disposed within the recess 70), the particles remain aligned with the nozzle while the air spreads out to flow over the impaction surface. Therefore, the two sections of the collection cup 60—the inner cup portion 62 and the trough portion 64—minimize water vapor condensation on the impaction surface and avoid or minimize dilution of the final collected sample. The area of the impaction surface is thus minimized, while maintaining sufficient dimensions for the platform holding it to provide adequate heat transfer to an underlying chiller, which maintains the layer of ice at or below a desired temperature. Water vapor remaining in the air stream passing through the nozzle and flowing over the cold impaction surface tends to condense on the surface as well as any cold surfaces that are connected to the impaction surface. Thus, the final sample is collected on the ice layer disposed in the recess 70 of the inner cup portion 62, and excess condensed water vapor is removed from the inner cup portion 62 and instead tends to accumulate in the trough portion 64 of the collection cup 60. The conical configuration of the inner cup portion 62 minimizes the total volume of ice required to form a flat impaction ice layer, and also aids in removal of the frozen ice sample, e.g., such as by melting and then flowing through an exit channel 78 in some implementations (e.g., for entrance into a LOC) such as shown in FIG. 6A, or by manual extraction via a pipette tip. The outer cup or trough portion 64 allows water vapor condensing on cold surfaces surrounding the impaction surface in the inner cup portion 62 to be drained away from the impaction ice layer and prevented from entering the collected sample as it is melted for recovery by pipette or transfer (e.g., such as to a LOC channel).

The advanced aerosol collection system S3 provides for greater water vapor extraction using virtual impaction of the aerosol particles after they are grown via condensation in the chilled laminar flow passage(s), in addition to ducting water away from the gaseous fluid flow using a flow divider baffle system(s) in the water extraction regions of the primary and secondary flow passages 16, 34. Thus, the advanced system S3 incorporates one, two or multiple steps of vapor removal by condensation and virtual impaction followed by impaction onto a layer of ice. In addition, the advanced system S3 incorporates a fluid flow conditioning process in which the minor flow from each VI, which contains the EBA, is further cooled by a chilled laminar flow passage(s) before impaction on ice. The virtual impaction steps (e.g., as shown in FIGS. 3 and 5) allow for minimal flow and water vapor contact with the ice impaction substrate, resulting in final ice sample volumes of 10 μL or less. Further, on or more size selection impactor(s) (e.g., size selection impactor 31 or size selection VI 32) provide for size separation of aerosol particles into two or more size fractions prior to water vapor extraction and sample collection. Thus, multiple size fractions can each be collected in separate cryogenic impactors, thereby allowing characterization of the size distribution of biomarkers in EBA.

It should be understood that the present invention is not limited to the specific configurations and numbers of chilled laminar flow passages and/or impactors of the exemplary embodiments. In accordance with the methodologies of the present invention, an aerosol collection system may include two or more chilled laminar flow passages in series and/or in parallel along a flow passage. For example, a system including three, four, five, six, or more chilled laminar flow passages may be provided in series or in parallel. In addition, the aerosol collection system may include two or more size selection virtual impactors and/or two or more concentrator virtual impactors in series and/or in parallel along the flow passage. In one embodiment, each laminar flow chilled passage is associated with a concentrator virtual impactor. Thus, the gaseous fluid is directed through a flow passage and into a first laminar flow chilled passage and then a first associated concentrator VI; the gaseous fluid is then directed from the first concentrator VI to a second laminar flow chilled passage and then a second associated concentrator VI; the gaseous fluid may then be directed from the second concentrator VI to a third laminar flow chilled passage and then third concentrator VI, and so forth. In other embodiments, the aerosol collection system includes two or more laminar flow chilled passages in series and/or in parallel; however, a concentrator VI may not be associated with each laminar flow chilled passage (e.g., thus, the gaseous fluid may pass from a first laminar flow chilled passage, and then into and through a second laminar flow chilled passage without an intermediate concentrator VI therebetween. For example, the exemplary device shown in FIG. 2 comprises five parallel laminar flow chilled passages in parallel and is otherwise configured similar to the configuration shown in FIG. 1. Preferably, however, the disclosed systems include at least one laminar flow chilled passage and at least one concentrator VI. In all embodiments, the arrangement and length of the laminar flow chilled passage(s) and/or concentrator VI(s) should decrease the temperature an amount sufficient to condense water vapor in the gaseous fluid flow into liquid water on the interior surface(s) of the laminar flow passage, and additionally condense water vapor onto the aerosol particles in order to grow the particles to a sufficient size for increasing inertia and impaction velocity (e.g., preferably to an aerodynamic diameter of at least about 1 μm). Furthermore, in preferred embodiments, the systems include multiple parallel laminar flow chilled tubular passages or other geometries to ensure sufficient cross-sectional area of the flow passage to maintain laminar flow while maintaining sufficiently small distances for flow of heat and water vapor to achieve optimal water vapor extraction and particle growth.

In addition, heating of the inlet portion 10 (e.g., the mouthpiece 12 and/or associated tubing), combined with a supply of heated humidified air (if necessary for the environment), allows maintenance of EBA droplet/particle size for improved accuracy in size determination using a parallel droplet counting system and during size separation. Measurement of the droplet sizes before condensation growth allows for calculation of the total volume of respiratory droplets collected. In an unheated system, a correction factor may be applied to adjust for changes in particle size depending on ambient temperature. By dividing the quantity of biomarker detected by the volume of respiratory fluid droplets collected, the disclosed systems allow for measurement of the concentration of biomarker in each subject's respiratory lining layer. Because individuals vary greatly in the number and size distribution of droplets generated (e.g., see Papineni, S R and Rosenthal, FS (1997) "*The size distribution of droplets in the exhaled breath of healthy human subjects*," J. Aerosol. Med. Off. J. Int. Soc. Aerosols. Med., 10(2):105-116; Edwards, D A et al. (2004) "*Inhaling to mitigate exhaled bioaerosols*," Proc. Natl. Acad. Sci. USA 101(50):17383-17388), crude measurement of biomarker quantity would be misleading, implying that a subject with few droplets and a very small total droplet volume had less biomarker in his or her respiratory tract, when he or she may actually have a much higher concentration of biomarker, simply masked by the difference in output of droplets.

The disclosed aerosol collection systems provide for efficient condensation growth of exhaled breath while reducing the temperature of the breath from about 37° C. to less than about 5° C., and in some embodiments to near or below 0° C. In addition, excess water vapor is effectively removed by condensation without dilution of the aerosol sample, followed by impaction achieved by acceleration of the aerosol particles through a nozzle directed onto a relatively thin layer of ice maintained at extremely low temperatures (e.g., between about −10° C. and about −16° C.). Final ice volumes of about 250 μL, or about 25 μL, or about 10 μL, or even 2.5 μL or less, may be achieved utilizing the disclosed systems and methodologies disclosed herein.

Data from EBA sampling and protein recovery using the disclosed methodologies is presented below. It should be understood however that the examples and information presented below are provided by way of further illustration and are not intended to be limiting of the present invention.

Aerosol Sampling and Protein Recovery

Protein recovery from eleven 30-minute samples from six subjects utilizing an EBA collection system in accordance with the present invention (without the optional 2.5 μm size selection VI) is presented in Table 1 below.

TABLE 1

Protein Recovery from Ice Impaction of 30-min EBA Collections

| Participate | Sample No. | Amount of Protein (μg) | Type of Collection | Volume of Liquid (mL) |
|---|---|---|---|---|
| 1 | 11901 | 44 | Ice | 1.2 |
| 1 | 13300 | 15 | Ice | 0.8 |

TABLE 1-continued

Protein Recovery from Ice Impaction of 30-min EBA Collections

| Participate | Sample No. | Amount of Protein (μg) | Type of Collection | Volume of Liquid (mL) |
|---|---|---|---|---|
| 2 | 11881 | 0 | Ice | 0.5 |
| 2 | 13280 | 37 | Liquid/Ice | <0.5 |
| 3 | 11871 | 8 | Ice | 1.5 |
| 3 | 13290 | 41 | Ice | 1.5 |
| 8 | 12717 | 0 | Ice | 0.5 |
| 8 | 13610 | 39 | Ice | 0.6 |
| SY | SY | 18 | Ice | 0.75 |
| SY | 13259 | 44 | Ice | NR |
| SY/LG | 13258 | 11 | Ice | NR |
| Mean (SD) | | 23 (18) | | |

Referring to Table 1, each sample was assayed for protein after lyophilization of the ice and reconstitution in 100 μL of 50 mM ammonium bicarbonate (as described in further below). The mean protein recovery 23 μg per 30-min sample (0.77 μg/min, approximately 200 L of exhaled breath per 30-min, or 115 ng protein/liter of exhaled breath) is substantially more efficient than reported in prior systems. In some implementations, the system provided for an inline size selection impactor that removed particles greater than about 2.5 μm from the final sample.

For example, Bredbert et al. (see Bredbert, A. et al. (2012) "Exhaled endogenous particles contain lung proteins," Clin. Chem. 58(2):431-440) reported protein recovery of 0.1 μg from 300 L of exhaled breath (0.33 ng/L or 0.002 μg/min) utilizing the system described in U.S. Patent Application Publication No. 2010/0297635 to Olin et al. Thus, the system of the present invention demonstrated an efficiency of about 350 times greater as compared to the system described in the '635 patent application to Olin et al. Whereas the Olin et al. device collected only particles larger than 0.5 μm in aerodynamic diameter and less than 2.0 μm, the disclosed systems of the present invention were able to collect a wide range of particle sizes, e.g., from about 0.005 μm in diameter and larger with the upper size range determined only by the inlet efficiency of the mouthpiece and flexible tubing for the human interface (about 20 μm). Moreover, the Olin et al. device collects sample on a solid dry substrate, which necessitates extraction from the surface and results in losses depending on the type of surface (hydrophilic or hydrophobic) and depending on the solvent used. The systems of the present invention avoid such problems, which are inherent to many conventional systems such as the Olin device.

Muccilli et al. (see Muccilli, V. et al. (2015) "Protein profile of exhaled breath condensate determined by high resolution mass spectrometry," J. Phann. Biomed. Anal., 105:134-149) reported recovery of about 50 μg of protein from a composite sample from 9 participants, each providing two 10-15 min samples using an EBC system (Turbo DECCS 09, MEDIVAC, Parma, Italy). Thus, it may be estimated that Muccilli et al. recovered approximately 0.2 μg/min from each subject on average. In contrast, the disclosed systems of the present invention demonstrated an average collection of about 0.77 μg/min, representing an approximately 4-fold improvement in protein recovery as compared to that reported by Muccilli et al. Moreover, Muccilli et al. reported that their collection methodology produced a sample diluted in 65 mL of water. Thus, their sampling method produced a dilute sample with a protein concentration of about 0.77 μg/mL. In contrast, samples collected using the disclosed systems of the present invention demonstrated an average protein concentration of about 28 μg/mL. Thus, the systems and methods of the present invention produced samples that were more substantially more concentrated (e.g., 36 times more concentrated) as compared to samples reported by Muccilli et al. and other prior systems. The substantial increase in concentration of sample achieved by the disclosed systems herein greatly enhances the utility of the collected sample as a front end for biomarker detection from exhaled breath.

Protein Analysis of Exhaled Breath Collected for 114 Min

An exhaled breath sample collected on ice for a total period of 114 min (pooled of 2 collections of 30 min, 1 collection of 14 min, 2 collections of 20 min) provided by the breath collection team. The samples were lyophilized and reconstituted in 100 μL of 50 mM ammonium bicarbonate. Using a colorimetric assay (Pierce BCA assay kit), it was determined that the sample contained 113 μg of total protein.

Figure 7:
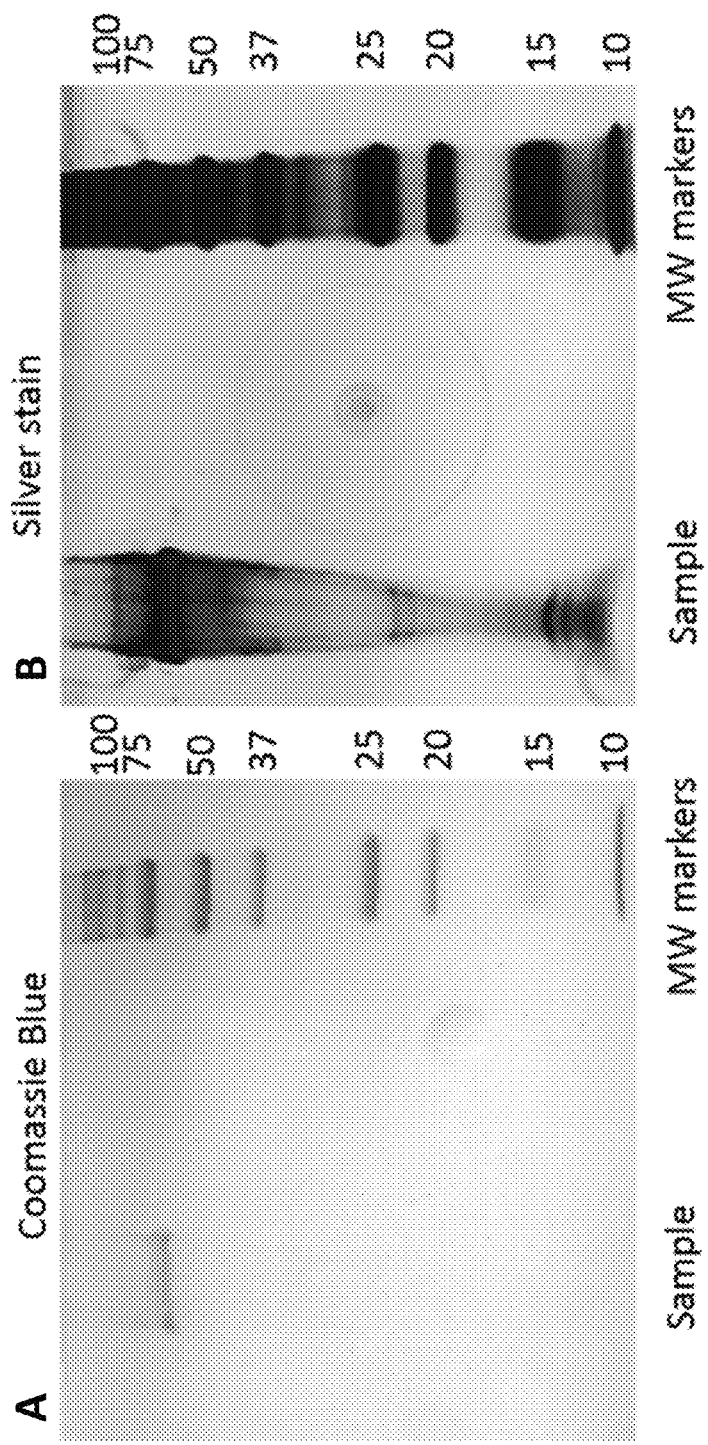
FIG. 7 are images showing sodium dodecyl sulfate polyacrylamide gel electrophoresis (SDS-PAGE) of a 20 μg exhaled breath aliquot stained with Coomassie blue (Panel A) and silver stain (Panel B).

A 20 μg aliquot was separated using a SDS-PAGE gel (8-16% polyacrylamide gel). This strategy was selected as separation is expected to offer a higher number of protein identifications. The Coomassie blue (CB) and silver stained (SS) gels are shown in FIG. 7. The CB stain shows a high mass band of molecular weight close to that of keratins. The SS gel shows several bands with molecular weights <15 KDa. It is possible that other proteins may be present at concentrations below the SS gel limit of detection (0.25 ng per band) and detectable in LCMS/MS analysis but not visible. In-gel tryptic digestion was performed (see Shevchenko, A. et al. (2006) "In-gel digestion for mass spectrometric characterization of proteins and proteomes," Nat. Protoc. 1(6):2856-2860). LC-MS/MS analysis of 16 gel bands was performed, representing the entire lane. The spectra acquired for the 16 gel bands were searched against the Uniprot Homo Sapiens database using MASCOT and SEQUEST search engines in Proteome Discoverer 2.1 (PD 2.1). Results were combined and protein FDR<1% were reported. Strong identifications required the presence of two unique peptides with peptide FDR<5%, and protein FDR<1%; weaker identifications required the presence of one unique peptide with peptide FDR<1%.

A total of 128 proteins were identified (see Table 2 below), with 27 proteins having strong identifications and 101 proteins having weaker identifications. Twenty-four proteins of the 128 proteins identified were previously identified (see Muccilli, V. et al. (2015) "Protein profile of exhaled breath condensate determined by high resolution mass spectrometry," J. Phann. Biomed. Anal., 105:134-149; Bredbert, A. et al. (2012) "Exhaled endogenous particles contain lung proteins," Clin. Chem. 58(2):431-440). Of the proteins identified. keratin 1, 2, 4, 5, 9, 10, 13, 14, 16, 80 and 6B were identified. It was demonstrated that background samples of filtered air had no detectable proteins by BCA assay; hence, they are likely introduced into the system during breath collection. Note that Muccilli et al. also reported cytokeratins, and estimated that these are the most abundant proteins in the exhaled breath sample. Furthermore, airway derived keratins are known to be important in certain forms of occupational asthma (see Wisnewski, A. V. et al. (2000) "Identification of human lung and skin proteins conjugated with hexamethylene diisocyanate in vitro and in vivo," Am. J. Respir. Crit. Care Med., 162(6):2330-2336). Note that an immunoglobulin (IgG H chain) was also identified, with the identification supported by one peptide.

TABLE 2

Identified Proteins by MASCOT and SEQUEST in PD 2.1. Proteins previously reported in exhaled breath are marked (*).

| Uniprot Accession # | Description | Coverage | # Unique Peptides | MW [kDa] |
|---|---|---|---|---|
| H6VRG2 | Keratin 1* | 60.9 | 30 | 66 |
| P35527 | Keratin, type I cytoskeletal 9* | 60.7 | 30 | 62 |
| P35908 | Keratin, type II cytoskeletal 2 epidermal* | 58.5 | 23 | 65.4 |
| P13645 | Keratin, type I cytoskeletal 10* | 55.3 | 23 | 58.8 |
| P13647 | Keratin, type II cytoskeletal 5* | 33.2 | 10 | 62.3 |
| P19013 | Keratin, type II cytoskeletal 4* | 33.5 | 9 | 57.3 |
| P02533 | Keratin, type I cytoskeletal 14* | 43.9 | 7 | 51.5 |
| A8K2H9 | highly similar to Homo sapiens keratin 13 (KRT13)* | 26.4 | 7 | 49.5 |
| D1MGQ2 | Alpha-2 globin chain | 57 | 7 | 15.2 |
| B4DPP6 | highly similar to Serum albumin* | 14.6 | 6 | 70.3 |
| Q86YZ3 | Hornerin* | 8.4 | 6 | 282.2 |
| B2R5B3 | Histone H2A* | 49.2 | 4 | 14.1 |
| D9YZU5 | Hemoglobin, beta* | 70.1 | 4 | 16 |
| P62979 | Ubiquitin-40S ribosomal protein S27a | 28.2 | 4 | 18 |
| P15924 | Desmoplakin* | 2.3 | 4 | 331.6 |
| Q02413 | Desmoglein-1* | 4.1 | 3 | 113.7 |
| P04083 | Annexin A1* | 11.8 | 3 | 38.7 |
| P81605-2 | Isoform 2 of Dermcidin | 20.7 | 3 | 12.4 |
| Q6UWP8 | Suprabasin* | 9.2 | 2 | 60.5 |
| P63261 | Actin, cytoplasmic 2 | 7.5 | 2 | 41.8 |
| Q6KB66-3 | Isoform 3 of Keratin, type II cytoskeletal 80* | 7 | 2 | 54.1 |
| B2R9F5 | cDNA, FLJ94365 | 4.4 | 2 | 86.6 |
| Q6ZWG9 | cDNA FLJ41103 fis, clone BLADE2005459 | 17.5 | 2 | 22.5 |
| P12273 | Prolactin-inducible protein* | 18.5 | 2 | 16.6 |
| P04259 | Keratin, type II cytoskeletal 6B* | 34.4 | 2 | 60 |
| V9HW31 | ATP synthase subunit beta | 5.5 | 2 | 56.5 |
| P05109 | Protein S100-A8* | 23.7 | 2 | 10.8 |
| Q8IYW2 | Protein CFAP46 | 1.5 | 1 | 303.3 |
| P11171 | Protein 4.1 | 1 | 1 | 97 |
| B4E0I1 | cDNA FLJ51422, highly similar to Interleukin-9 receptor | 11.6 | 1 | 36.7 |
| P42701 | Interleukin-12 receptor subunit beta-1 | 5.7 | 1 | 73.1 |
| Q92545 | Transmembrane protein 131 | 0.6 | 1 | 205 |
| A0A088AWL3 | Nuclear receptor corepressor 1 | 0.6 | 1 | 258.8 |
| P08235-3 | Isoform 3 of Mineralocorticoid receptor | 1.4 | 1 | 107.5 |
| A8K7H3 | cDNA FLJ77670, highly similar to Homo sapiens ribosomal protein S15a (RPS15A), mRNA | 15.4 | 1 | 14.8 |
| Q96DA0 | Zymogen granule protein 16 homolog B* | 7.7 | 1 | 22.7 |
| P00915 | Carbonic anhydrase 1 | 6.1 | 1 | 28.9 |
| P53355-3 | Isoform 3 of Death-associated protein kinase 1 | 2.6 | 1 | 161.1 |
| P59542 | Taste receptor type 2 member 19 | 13 | 1 | 33.9 |
| I6L9B7 | WDR85 protein | 15.4 | 1 | 25.5 |
| A8KAP9 | highly similar to Homo sapiens argininosuccinate synthetase (ASS) | 5.1 | 1 | 46.5 |
| Q9ULK2-2 | Isoform 2 of Ataxin-7-like protein 1 | 28.1 | 1 | 16.2 |
| F4MHF8 | Ubiquitously transcribed tetratricopeptide repeat protein Y-linked transcript variant 279 | 1.6 | 1 | 67.9 |
| B2R4M6 | Protein S100 | 13.2 | 1 | 13.2 |
| H7C2V2 | Ankyrin repeat and IBR domain-containing protein 1 (Fragment) | 7.4 | 1 | 18.3 |
| Q4VAT4 | GLP2R protein (Fragment) | 6.5 | 1 | 63 |
| Q9UHL9-3 | Isoform 3 of General transcription factor II-I repeat domain-containing protein 1 | 1.2 | 1 | 107.9 |
| Q9NZT1 | Calmodulin-like protein 5* | 15.8 | 1 | 15.9 |
| O75197 | Low-density lipoprotein receptor-related protein 5 | 2.7 | 1 | 179 |
| Q96N11 | Uncharacterized protein C7 or f26 | 5.1 | 1 | 50 |
| P08F94 | Fibrocystin | 0.8 | 1 | 446.4 |
| Q9C0E8-4 | Isoform 4 of Protein lunapark | 3.1 | 1 | 50.8 |
| Q8IYI6 | Exocyst complex component 8 | 2.5 | 1 | 81.7 |
| P39059 | Collagen alpha-1(XV) chain | 3.2 | 1 | 141.6 |
| Q96E16 | Small integral membrane protein 19 | 41.1 | 1 | 12.4 |
| A0A087X1N7 | Nebulin | 0.4 | 1 | 990.2 |
| P35125 | Ubiquitin carboxyl-terminal hydrolase 6 | 3 | 1 | 158.6 |
| Q8NG31 | Protein CASC5 | 1 | 1 | 265.2 |
| B4DVU9 | highly similar to Heat shock 70 kDa protein 1* | 5 | 1 | 59.1 |

TABLE 2-continued

Identified Proteins by MASCOT and SEQUEST in PD 2.1. Proteins previously reported in exhaled breath are marked (*).

| Uniprot Accession # | Description | Coverage | # Unique Peptides | MW [kDa] |
|---|---|---|---|---|
| Q9BQG2 | Peroxisomal NADH pyrophosphatase NUDT12 | 3.9 | 1 | 52 |
| Q16195 | Keratin (Fragment) | 35.7 | 1 | 27.6 |
| Q5THJ4 | Vacuolar protein sorting-associated protein 13D | 1 | 1 | 491.6 |
| K7EIL9 | Histone chaperone ASF1B | 49.4 | 1 | 9.2 |
| P08779 | Keratin, type I cytoskeletal 16* | 40 | 1 | 51.2 |
| A0A096LNL5 | Cytochrome P450 26C1 | 6.3 | 1 | 32.6 |
| B8K2F8 | UDP-glucuronosyltransferase 1A4 (Fragment) | 76.3 | 1 | 6.5 |
| S6BAQ4 | IgG H chain | 17.8 | 1 | 25.3 |
| Q8TCD0 | Uncharacterized protein | 8.4 | 1 | 26.2 |
| Q6TFL3-4 | Isoform 3 of Coiled-coil domain-containing protein 171 | 2.2 | 1 | 153.6 |
| Q96FS4 | Signal-induced proliferation-associated protein 1 | 3.6 | 1 | 112.1 |
| A0A075B6Z2 | Protein TRAJ56 (Fragment) | 38.1 | 1 | 2.2 |
| A7BI36 | p180/ribosome receptor | 1.7 | 1 | 165.6 |
| P53778 | Mitogen-activated protein kinase 12 | 10.6 | 1 | 41.9 |
| P02808 | Statherin | 48.4 | 1 | 7.3 |
| Q9NYV4 | Cyclin-dependent kinase 12 | 2.8 | 1 | 164.1 |
| Q13099-3 | Isoform 3 of Intraflagellar transport protein 88 homolog | 3.9 | 1 | 92.3 |
| A7E2Y5 | DnaJ (Hsp40) homolog, subfamily C, member 13 | 1.8 | 1 | 254.3 |
| Q6PJG9 | Leucine-rich repeat and fibronectin type-III domain-containing protein 4 | 5.5 | 1 | 66.8 |
| Q9NQT8 | Kinesin-like protein KIF13B | 0.7 | 1 | 202.7 |
| Q6ZMZ0 | E3 ubiquitin-protein ligase RNF19B | 5.6 | 1 | 77.9 |
| Q59F72 | Proteasome alpha 6 subunit variant (Fragment) | 52.5 | 1 | 8.9 |
| P29475-5 | Isoform 5 of Nitric oxide synthase, brain | 1 | 1 | 164.7 |
| Q6ZUM4 | Rho GTPase-activating protein 27 | 5.7 | 1 | 98.3 |
| Q9Y6T7 | Diacylglycerol kinase beta | 4.4 | 1 | 90.5 |
| Q6Q759 | Sperm-associated antigen 17 | 0.5 | 1 | 251.6 |
| Q9GZZ8 | Extracellular glycoprotein lacritin | 8 | 1 | 14.2 |
| I3L4V6 | Nucleoredoxin (Fragment) | 7.4 | 1 | 26 |
| Q8N1C8 | HSPA9 protein (Fragment) | 1.3 | 1 | 73.8 |
| A5YRU9 | MUC1 isoform T9 | 32.7 | 1 | 12.1 |
| Q9HA77 | Probable cysteine--tRNA ligase, mitochondrial | 3.7 | 1 | 62.2 |
| Q9BYB0 | SH3 and multiple ankyrin repeat domains protein 3 | 1.7 | 1 | 184.6 |
| F8VWW7 | SPRY domain-containing protein 3 | 8.1 | 1 | 53.8 |
| Q12852-2 | Isoform 2 of Mitogen-activated protein kinase kinase kinase 12 | 4.7 | 1 | 96.3 |
| P14625 | Endoplasmin | 4.1 | 1 | 92.4 |
| Q96Q05-2 | Isoform 2 of Trafficking protein particle complex subunit 9 | 3.3 | 1 | 139.3 |
| Q5TH69 | Brefeldin A-inhibited guanine nucleotide-exchange protein 3 | 1.1 | 1 | 240.5 |
| D6W593 | THUMP domain containing 2, isoform CRA_b | 3.4 | 1 | 56.4 |
| Q15019-2 | Isoform 2 of Septin-2 | 7.6 | 1 | 45.4 |
| Q9NYQ6 | Cadherin EGF LAG seven-pass G-type receptor 1 | 1.1 | 1 | 329.3 |
| Q68DQ2 | Very large A-kinase anchor protein | 1.3 | 1 | 330.4 |
| E7BWS0 | KIR2DL1 | 7.8 | 1 | 38.6 |
| P51955 | Serine/threonine-protein kinase Nek2 | 4.7 | 1 | 51.7 |
| Q9H0E7 | Ubiquitin carboxyl-terminal hydrolase 44 | 2 | 1 | 81.1 |
| Q5D862 | Filaggrin-2* | 0.5 | 1 | 247.9 |
| Q9BXM7 | Serine/threonine-protein kinase PINK1, mitochondrial | 7.4 | 1 | 62.7 |
| P08240 | Signal recognition particle receptor subunit alpha | 6.9 | 1 | 69.8 |
| A0A024R6X1 | Carboxylesterase 2 (Intestine, liver), isoform CRA_b | 6.9 | 1 | 68.9 |
| A0A075X6V8 | Cytochrome b (Fragment) | 12.9 | 1 | 33.2 |
| F5H7F8 | Ras-related protein Rab-35 | 22.4 | 1 | 16.4 |
| B2R7K0 | cDNA, FLJ93477, highly similar to Homo sapiens G protein-coupled receptor kinase 5 (GRK5), mRNA | 6.4 | 1 | 67.7 |
| P60893 | Probable G-protein coupled receptor 85 | 11.4 | 1 | 42 |
| Q4LE38 | IKBKAP variant protein (Fragment) | 2.8 | 1 | 151.4 |

TABLE 2-continued

Identified Proteins by MASCOT and SEQUEST in PD 2.1. Proteins previously reported in exhaled breath are marked (*).

| Uniprot Accession # | Description | Coverage | # Unique Peptides | MW [kDa] |
|---|---|---|---|---|
| O15119 | T-box transcription factor TBX3 | 4.7 | 1 | 79.3 |
| P50748 | Kinetochore-associated protein 1 | 1.7 | 1 | 250.6 |
| Q8WVJ2 | NudC domain-containing protein 2 | 12.7 | 1 | 17.7 |
| X5D9A5 | Paired-like homeodomain 1 isoform A (Fragment) | 12.7 | 1 | 34.1 |
| L0R5A1 | Alternative protein CSF2RB | 7.4 | 1 | 11.6 |
| Q8NFI3 | Cytosolic endo-beta-N-acetylglucosaminidase | 1.9 | 1 | 83.9 |
| A0A087WZE4 | Spectrin alpha chain, erythrocytic 1 | 1.5 | 1 | 280.9 |
| A0A024R3S6 | HCG1984338, isoform CRA_a | 25.3 | 1 | 16.9 |
| Q96T92 | Insulinoma-associated protein 2 | 3 | 1 | 59.5 |
| Q0IIN1 | Keratin 77 | 4.2 | 1 | 61.8 |
| Q8TF72 | Protein Shroom3 | 0.5 | 1 | 216.7 |
| F8WEC6 | Peroxisomal membrane protein PMP34 | 18.9 | 1 | 16.4 |
| B2R853 | cDNA, FLJ93744, highly similar to Homo sapiens keratin 6E (KRT6E), mRNA | 39.9 | 1 | 60 |
| Q8N690-2 | Isoform 2 of Beta-defensin 119 | 31.8 | 1 | 10.1 |
| P58340-3 | Isoform 3 of Myeloid leukemia factor 1 | 11.4 | 1 | 33.9 |
| Q5SXM2 | snRNA-activating protein complex subunit 4 | 2.8 | 1 | 159.3 |

Discussion

Conventional EBC collection devices attempt to condense all or a large portion of the water vapor in breath on the walls of the device, as the breath flows over the cool walls of the device (e.g., usually within a tube). Sometimes the tube is convoluted and typically the air flow is turbulent after passing through a valve. In all cases, the primary means of collection in such EBC collection devices is condensation of vapor in the breath on the walls of the device, with the generation and collection of as much of the EBC as possible desired. In such EBC devices, the walls are cooled in order to enhance and promote vapor condensation and any breath aerosol that is collected is mixed with and extensively diluted by the condensed water vapor.

In contrast, the disclosed systems of the present invention discard essentially all or most of the breath condensate (water vapor from breath), and instead collect primarily only aerosol droplets or particles. Thus, the disclosed systems seek to purposely discard essentially all of the breath condensate (i.e. exhaled water vapor) that condenses on the walls of the device. In accordance with disclosed embodiments, water vapor that condenses on the walls is ducted away from the sample using a flow divider system. The collected sample is almost entirely EBA particles. Exhaled aerosol droplets are grown by condensing a few femto-liters of water vapor on the aerosol droplets to increase their size while removing water vapor condensed on cold surfaces in the system using chillers and operably associated flow divider systems. Water vapor that did not condense may also be removed via one or more virtual impactors. Thus, the water vapor utilized to grow the aerosol particles is negligible with regard to effecting concentration, but sufficient for increasing inertia of the aerosol particles in the air stream and for impaction. The disclosed systems limit unwanted condensation of water vapor on the ice impaction surface by extracting condensed water vapor using a flow divider baffle system, thus drying the airstream and chilling it, preferably chilled to near 0°, thereby reducing the water vapor content, followed by concentration of aerosol by virtual impaction so that only about 10% of the near 0° C. air is exposed to the cryogenic impaction surface. Thus, the cryogenic impaction surface collects aerosol droplets on a layer of ice (e.g., including a volume of less than 500 μL preferably less than 100 μL, more preferably about 10 μL, or about 2.5 μL or less), enabled by cooling the gaseous fluid flow and removing excess water vapor via laminar flow chilled passage(s) and/or concentrating aerosol particles in a smaller volume of gaseous fluid via one of more VI(s). In some embodiments, successive cycles of drying and concentration are provided in order to achieve microliter scale final volumes of ice containing virtually all of the exhaled breath aerosol. Thus, the disclosed systems may be utilized in conjunction with a chip (LOC) device compatible with ice impaction.

Thus, the disclosed systems are exhaled breath aerosol (EBA) collectors as opposed to EBC collectors. Unlike the devices for aerosol growth disclosed in U.S. Pat. Nos. 6,712,881 and 8,801,838 to Hering, S. V. et al., the water vapor is not injected into the air stream with a heated "initiator" element. Rather, the incoming air stream in the disclosed systems is already saturated and only needs to be cooled. Similarly, and unlike the device disclosed in U.S. Pat. No. 8,250,903 to McDevitt, J. et al., steam need not be injected into the air flow, because the air stream is already saturated. The disclosed systems are configured to specifically discard as much of the EBC as possible, and instead collect only or primarily aerosol droplets.

However, as a general aerosol collector, a system such as that disclosed in U.S. Pat. Nos. 6,712,881 and 8,801,838 to Hering, S. V. et al., could be utilized in conjunction with the disclosed systems herein, wherein the water vapor extraction and aerosol concentration techniques utilized in the systems of the present invention, along with impaction on a layer of ice, would substantially improve efficiency and aerosol concentration in the resulting sample in such systems. Thus, use of the systems and methods disclosed herein would allow for bioaerosol collection with: 1) increased impaction efficiency as compared to prior systems providing for impingement in liquid; 2) substantially increased aerosol concentration as compared with prior systems providing for impingement and dilution in liquid; and 3) preservation of labile biomolecules by immediate freezing; and 4) substantially reduced sample loss and damage as compared to prior systems providing for extraction from a solid collection surface (e.g. such as a filter, or metal, plastic, or silicon impaction surface).

Conventional EBC collectors use the force of the breath to propel the air stream through the collector. This results in extremely variable air flow rates, going from zero to a few liters per minute several times each minute. The aerosol collection properties of any collector are dependent on the rate of air flow. Thus, the aerosol collection efficiencies of EBC collectors vary substantially over the course of each breath.

In contrast with EBC collectors, the EBA collection devices of the present invention do not rely on the force of a subject's breathing to propel air through the device. Rather, the breath is pulled through the device with a pump that keeps the flow within the device moving at an extremely constant rate (e.g., instead of 100% variability, it is <<5% variability). This allows for the use of the 'nozzle to surface impactor' design, thereby achieving highly predictable and constant collection efficiencies throughout the subject's breathing cycle.

Thus, the systems and methods of the present invention, which provide for the collection of bioaerosols by impaction on ice, is a uniquely different approach having numerous advantages over prior art systems. As provided in the exemplary systems disclosed herein, the aerosol droplets are enlarged within the system by condensation growth. The tubes of the system are preferably straight and designed to produce a laminar air stream flow, so that turbulence is minimized or avoided and the EBA is not deposited on the walls of the device or mixed with the water vapor condensate. In contrast, turbulent flow is desired and encouraged in conventional EBC collectors in order to increase EBC condensation and mixing of the EBA into the EBC.

In the disclosed systems, aerosol flows out of the cold condensation growth tubes conveyed by a now chilled air stream via a nozzle, which directs the laminar flow at high velocity against a surface composed of a thin layer of ice. The layer of ice is maintained at a sufficiently low temperature so that the air stream from the nozzle does not melt the ice. In addition, the air stream is chilled by the condensation tubes prior to impaction on the ice, as noted above. No known conventional breath collection devices, or any known bioaerosol sampler, provide for the impaction of collected aerosol onto an ice surface, as provided in the present invention. The impacted aerosol is instantly frozen thereby preserving the labile molecules in the aerosol.

All identified publications and references are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. An aerosol collection system comprising:
    an inlet portion configured to receive a gaseous fluid containing water vapor and aerosol particles;
    a primary passage in fluid communication with said inlet portion and configured to channel a flow of said gaseous fluid therethrough;
    at least one laminar flow chilled passage in fluid communication with said primary passage, and configured to cool said gaseous fluid flow to a temperature sufficient to condense at least about 90% of said water vapor onto an interior surface of said laminar flow chilled passage;
    an outlet portion in fluid communication with said primary passage; and
    a flow-dividing baffle operably associated with said laminar flow chilled passage and configured to duct condensed water vapor on said interior surface of said laminar flow chilled passage away from said primary passage and said outlet portion;
    a sample collection region configured to receive from said outlet portion said aerosol particles, said sample collection region comprising a cooler device capable of maintaining a layer of ice at a desired temperature, wherein said aerosol particles are impacted onto said layer of ice in said sample collection region.

2. The system of claim 1, wherein a remaining portion of said water vapor condenses onto said aerosol particles and thereby increases aerodynamic diameter of said aerosol particles.

3. The system of claim 1, further comprising a size selection impactor in fluid communication with said primary passage and upstream from said laminar flow chilled passage, said size selection impactor configured to separate and remove said aerosol particles having a diameter greater than a preselected size away from said primary passage.

4. The system of claim 3, further comprising a secondary passage in fluid communication with said first size selection impactor, wherein said aerosol particles having a diameter greater than said preselected size flow into said secondary passage.

5. The system of claim 4, further comprising at least a second laminar flow chilled passage operably associated with said secondary passage and configured to cool said gaseous fluid flow in said secondary passage to a temperature sufficient to condense a portion of said water vapor onto an interior surface of said second laminar flow chilled passage.

6. The system of claim 5, further comprising a second flow-dividing baffle operably associated with said second laminar flow chilled passage and configured to duct condensed water vapor on said interior surface of said second laminar flow chilled passage away from said secondary passage.

7. The system of claim 5, further comprising at least one concentrator virtual impactor in fluid communication with said secondary passage and downstream from said second laminar flow chilled passage, said concentrator virtual impactor configured to divide said gaseous fluid flow into a major flow and a minor flow, wherein said aerosol particles are concentrated in said minor flow and a portion of said water vapor is directed into said major flow.

8. The system of claim 7, wherein said aerosol particles are concentrated at least about 10-fold in said minor flow.

9. The system of claim 5, wherein said secondary passage is in fluid communication with a second outlet portion, said second outlet portion downstream from said second laminar flow chilled passage, further comprising a second sample collection region configured to receive from said second outlet portion said aerosol particles, wherein said aerosol particles are impacted onto a layer of ice in said second sample collection region.

10. The system of claim 1, further comprising at least one concentrator virtual impactor in fluid communication with said primary passage and downstream from said laminar flow chilled passage, said concentrator virtual impactor configured to divide said gaseous fluid flow into a major flow and a minor flow, wherein said aerosol particles are concentrated in said minor flow and a portion of said water vapor is directed into said major flow.

11. The system of claim 10, which comprises a plurality of said concentrator virtual impactors in series and in fluid communication with said primary passage.

12. The system of claim 10, wherein said aerosol particles are concentrated at least about 10-fold in said minor flow.

13. The system of claim 1, further comprising a heating device upstream from said laminar flow chilled passage and configured to maintain said gaseous fluid flow in said primary passage at a temperature of about 37° C.

14. The system of claim 1, wherein said outlet portion comprises an acceleration nozzle configured to increase velocity of said aerosol particles for impaction onto said layer of ice.

15. The system of claim 1, further comprising a droplet counting system operably associated with said primary passage and configured to determine number and size distribution of said aerosol particles.

16. The system of claim 1, wherein said layer of ice has a volume of between about 2.5 μL to about 1500 μL.

17. The system of claim 1, wherein said cooler device is configured to maintain said layer of ice at a temperature of between about −1° C. and about −20° C.

18. The system of claim 1, further comprising a pressure equalization device upstream from said laminar flow chilled passage, said pressure equalization device comprising a filter system and a supply channel in fluid communication with said primary passage and configured to supply a filtered, pressure-equalized air stream into said primary passage.

19. The system of claim 18, wherein said pressure equalization device comprises a 1-way valve configured to maintain a unidirectional flow of said pressure-equalized air stream.

20. The system of claim 18, further comprising a 3-way valve in fluid communication with said primary passage and upstream from said pressure equalization device, said 3-way valve configured to channel extraneous material in said gaseous fluid flow out of said primary passage.

21. The system of claim 18, further comprising a humidifier operably associated with said primary passage.

22. The system of claim 1, further comprising an ultrasonic flow sensor device downstream from said inlet portion and configured to measure and monitor velocity and volume of said gaseous fluid flow in said primary passage.

23. The system of claim 1, further comprising a supply channel in fluid communication with said inlet portion and configured to inject humid, filtered air into said inlet portion, wherein said supply channel comprises a high efficiency particulate air (HEPA) filter.

24. The system of claim 23, further comprising a 1-way valve in fluid communication with said supply channel and configured to maintain a unidirectional flow of said gaseous fluid flow therethrough.

25. A method of collecting and analyzing aerosol particles from a gaseous fluid, comprising the steps of:
providing a primary passage comprising an inlet portion and an outlet portion, and a laminar flow chilled passage in fluid communication with said primary passage and intermediate said inlet portion and said outlet portion;
directing a flow of gaseous fluid from said inlet portion and through said laminar flow chilled passage toward said outlet portion, said flow of gaseous fluid comprising water vapor and aerosol particles;
cooling said gaseous fluid flow in said laminar flow chilled passage to a temperature sufficient to condense at least about 90% of said water vapor onto an interior surface of said laminar flow chilled passage;
ducting said condensed water vapor on said interior surface of said laminar flow chilled passage away from said primary passage and said outlet portion; and
directing said aerosol particles from said laminar flow chilled passage through said outlet portion; and
impacting said aerosol particles from said outlet portion onto a layer of ice, thereby forming a frozen sample comprising said aerosol particles.

26. The method of claim 25, comprising the further steps of:
melting said frozen sample; and
detecting one or more biomarkers in said melted sample.

27. The method of claim 26, wherein said biomarkers are associated with a respiratory disease, disorder or infection.

28. The method of claim 25, comprising the further step of directing said aerosol particles and said remaining portion of said water vapor from said laminar flow chilled passage through a concentrator virtual impactor prior to said step of directing said aerosol particles through said outlet portion, wherein a minor flow from said concentrator virtual impactor containing said aerosol particles is directed through said outlet portion.

29. The method of claim 25, wherein said layer of ice is maintained at a temperature of between about −1° C. and about −20° C.

30. The method of claim 25, wherein said frozen sample has a volume of between about 2.5 μL to about 1500 μL.

* * * * *